US010927386B2

(12) United States Patent
Brugmans et al.

(10) Patent No.: US 10,927,386 B2
(45) Date of Patent: Feb. 23, 2021

(54) COMPOSITIONS AND METHODS FOR PERONOSPORA RESISTANCE IN SPINACH

(71) Applicant: SEMINIS VEGETABLE SEEDS, INC., St. Louis, MO (US)

(72) Inventors: Bart Willem Brugmans, Beek en Donk (NL); John Meeuwsen, Bennekom (NL); Claudia Nooyen, Wageningen (NL)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 168 days.

(21) Appl. No.: 14/632,871

(22) Filed: Feb. 26, 2015

(65) Prior Publication Data
US 2015/0240256 A1 Aug. 27, 2015

Related U.S. Application Data

(60) Provisional application No. 61/945,675, filed on Feb. 27, 2014.

(51) Int. Cl.
C12N 15/82 (2006.01)
A01H 5/12 (2018.01)
C12Q 1/6895 (2018.01)

(52) U.S. Cl.
CPC ........... *C12N 15/8279* (2013.01); *A01H 5/12* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 4,900,659 A * | 2/1990 | Lo .......................... C07K 14/22 435/6.15 |
| 7,935,864 B2 | 5/2011 | Baerends |
| 7,935,865 B2 | 5/2011 | Baerends |
| 7,935,866 B2 | 5/2011 | Baerends |
| 7,935,867 B2 | 5/2011 | Baerends |
| 7,935,868 B2 | 5/2011 | Baerends |
| 7,939,717 B2 | 5/2011 | Baerends |
| 7,939,718 B2 | 5/2011 | Baerends |
| 7,939,719 B2 | 5/2011 | Baerends |
| 7,939,720 B2 | 5/2011 | Baerends |
| 8,008,548 B2 | 8/2011 | DeWit et al. |
| 8,354,570 B2 | 1/2013 | Van Den Ackerveken et al. |
| 9,402,363 B1 * | 8/2016 | Feitsma ............... C12Q 1/6895 |
| 2006/0134663 A1 | 6/2006 | Harkin et al. |
| 2007/0016976 A1 | 1/2007 | Katagiri et al. |
| 2009/0300786 A1 * | 12/2009 | Baerends ................. A01H 5/12 800/268 |
| 2010/0115658 A1 | 5/2010 | Van Damme et al. |
| 2012/0107458 A1† | 5/2012 | den Braber |
| 2012/0216313 A1 | 8/2012 | den Braber |
| 2012/0222147 A1† | 8/2012 | Dijkstra |
| 2013/0036516 A1 | 2/2013 | Hatzfeld et al. |
| 2013/0055422 A1 * | 2/2013 | Baerends ................. A01H 5/12 800/260 |
| 2013/0055454 A1† | 2/2013 | den Braber |
| 2013/0055455 A1† | 2/2013 | den Braber |
| 2013/0055456 A1† | 2/2013 | den Braber |
| 2013/0198882 A1 * | 8/2013 | Baerends ................. A01H 5/12 800/260 |
| 2013/0198884 A1† | 8/2013 | Dijkstra |
| 2013/0205420 A1† | 8/2013 | Baerends |
| 2013/0230635 A1 * | 9/2013 | Den Braber ............. A01H 1/04 426/615 |
| 2013/0243931 A1 | 9/2013 | Baerends |
| 2014/0053293 A1 | 2/2014 | Den Braber |
| 2014/0068800 A1 | 3/2014 | den Braber |
| 2015/0020231 A1 * | 1/2015 | Baerends ................. A01H 5/12 800/260 |
| 2015/0082483 A1 | 3/2015 | Dijkstra |
| 2015/0082583 A1 * | 3/2015 | Hooper ................. F16B 5/0614 24/455 |
| 2015/0101073 A1 | 4/2015 | Brugmans et al. |
| 2016/0177330 A1 * | 6/2016 | Dijkstra ................. A01H 1/04 800/265 |
| 2017/0055481 A1 | 3/2017 | Brugmans et al. |
| 2017/0327839 A1 | 11/2017 | Feitsma et al. |

(Continued)

FOREIGN PATENT DOCUMENTS

| EP | 2 586 294 A1 | 5/2013 |
| JP | S56106567 A | 8/1981 |
| JP | S62179357 A | 8/1987 |

(Continued)

OTHER PUBLICATIONS

Amundadottir et al., Nature Genet 38(6):652-58 (2006).*
Lo et al., Int J Cancer 115:276-83 (2005).*
Polesskaya et al., J Neurosci Res 83:362-73 (2006).*
Irish et al., Plant Dis 91:1392-96 (2007).*
Correll et al., Eur J Plant Pathol 129:193-205 (2011).*
Irish et al., Phytopath 90(8):894-900 (2008).*
Lewis et al., AE004969.1 (2003).*
Tettelin et al., Sci 287:1809-15 (2000).*
Xu et al., Nat Commun 8:15275, doi: 10.1038/ncomms15275 (2017).*
Irish et al. (2008) Phytopath 90(8):894-900.*
Correll et al. (2011) Eur J Plant Pathol 129:193-205.*
Irish et al. (2007) Plant Dis 91:1392-96.*

(Continued)

*Primary Examiner* — Russell T Boggs
(74) *Attorney, Agent, or Firm* — Dentons US LLP

(57) ABSTRACT

The invention provides for spinach plants with broad-spectrum resistance to downy mildew disease and their progeny. Such plants may comprise unique combinations of alleles resulting in the broad-spectrum resistance to downy mildew. In certain aspects, compositions, including distinct polymorphic molecular markers, and methods for producing, using, identifying, selecting, and the like of plants or germplasm with resistance to downy mildew are provided.

21 Claims, 5 Drawing Sheets

Specification includes a Sequence Listing.

(56) References Cited

U.S. PATENT DOCUMENTS

2019/0127753 A1  5/2019  Kock et al.

FOREIGN PATENT DOCUMENTS

| | | |
|---|---|---|
| JP | 2008-502335 | 1/2008 |
| JP | 2008141994 A | 6/2008 |
| JP | 2009-513152 | 4/2009 |
| WO | WO 2005/124108 | 12/2005 |
| WO | WO 2007/051626 | 5/2007 |
| WO | 2013/064436 A1 | 5/2013 |
| WO | 2015036378 A1 † | 3/2015 |
| WO | WO2015/036378 * | 3/2015 |

OTHER PUBLICATIONS

Affidavit of A. Rijpkema regarding NZ Pat. App. No. 630170 (Oct. 10, 2016).*
Affidavit of J. Kniskern regarding NZ Pat. App. No. 630170 (Oct. 16, 2016).*
Further Amended Counterstatement regarding NZ Pat. No. 630710 (Nov. 14, 2017).*
Affidavit of R. J. Henry regarding NZ Pat. No. 630710 (Dec. 16, 2018).*
Tettelin et al. (2000) Sci 287:1809-15.*
Arumuganathan & Earle (1991) Plant Mal Biol Rep 9:208-18.*
Bentley et al., "Generation of an open pollinated near-isogenic spinach line with homozygous resistance to the downy mildew pathogen," *Phytopathology*, 96(6):S12, APS Annual Meeting, 2006 (abstract).
Brandenberger et al., "Evaluation of Spinach Germplasm for Resistance to a New Race (Race 4) of *Peronospora farinosa* f. sp. Spinaciae," HortScience, 27(20):1118-1119, 1992.
Brenner, "The US Spinach Germplasm Collection," presented at The T.E. Morelock International Spinach Conference, Fayetteville, AR 2009 (abstract).
Correll et al., "Quantitative resistance to race 6 of the downy mildew pathogen (*Peronosporia farinosa* f. sp. *Spinciae*) of spinach," *Phytopathology*, 90(6 Supp.):S16, 2000.
Correll et al., "Spinach: better management of downy mildew and white rust through genomics," Eur J Plant Pathol 129:193-205, 2011.
Eenink, "Linkage in spinacia-oleracea of two race specific genes for resistance to downy mildew *Peronospora farinosa*-f-sp spinaciae," Euphytica 25(3): 713-715, 1976.
Eenink, et al., Resistance in spinach (*Spinacia oleracea* L.) to false mildew (*Peronospora spinaciae Laub*), Zaadbelangen, 39(4):101-103, 1976.
Fernie et al., "Natural genetic variation for improving crop quality," Curr Opin Plant Biol 9:196-202, 2006.
Handke et al., "Detection of a linkage of the four dominant mildew resistance genes "M1M2M3M4" in spinach from the wildtype Spinacia turkestancia," Garetnbauwissenschaft 65(2):73-78, 2000 (English abstract).
Irish et al., "Molecular characterization of spinach germplasm and a marker linked to downy mildew resistance using AFLPs," Phytopathology 94(6):544, 2004 (abstract).
Irish, et al., "Three new races of the spinach downy mildew pathogen identified by a modified set of spinach differentials," Plant Disease, 91(11):1392-1396, 2007.
Irish et al., "Characterization of a resistance locus (Pfs-1) to the spinach downy mildew pathogen (*Peronosporia farinosa* f. sp. spinaciae) and development of a molecular marker linked to Pfs-1," Phytopathology 894-900, 2008.
Khattak et al., "A genetic linkage map of Spinacia oleracea and localization of a sex determination locus," Euphytica 148:311-318, 2006.
Kik et al., "The CGN Spinach Collection: Overview and Recent Collecting Expeditions," available at <spinach.uark.edu/Session%2011%PDFs/Chirs%20Kik.pdf>, 2011.
Mou et al., "Screening for resistance to leaf spot diseases of spinach," HortScience, 43(6):1706-1710, 2008.
Mou, "Leafminer resistance in spinach," HortScience 43(6):1716-1719, 2008.
Sadikhova, "Research and development of the vegetable system in Azerbaijan, In increasing market-oriented vegetable production in Central Asia and the caucasus through collaborative research and development," pp. 29-35, 2006.
Smith, "Embryo culture of a tomato species hybrid," *Pro Am Soc Hort Sci*, 44:413-16, 1944.
Stam, "Construction of integrated genetic linkage maps by means of a new computer package: JoinMap," Plant J 3:739-844, 1993.
Spinach varieties for industry crops, available at <http://www.rijkzwaan.com/wps/wcm/connect/rz+corporate/rijk+zwaan/products_and_services/products/industry/industry crops+english/spinach>, accessed on Aug. 20, 2015.
Yang et al., "Initial fine mapping of the spinach downy mildew resistance locus RPFI," University of Arkansas, 2013, 102 pages.
International Search Report and Written Opinion for PCT Application No. PCT/US14/59610, dated Feb. 3, 2015.
International Search Report for EP15156928, dated Jul. 20, 2015.
Leaflet for Spinach Field Day, Yuma, Arizona, dated 2013.
Leaflet for West Spinach Field Day, Salinas, California, dated 2014.
Batley et al., "SNP Applications in Plants," in Association Mapping in Plants, Oraguzie et al., eds. Springer, Berlin, 95-102, 2007.
Ganal et al., "SNP identification in crop plants," *Current Opinion in Plant Biology* 12:211-217, 2009.
Hallavant "The first archaeobotanical evidence of *Spinacia oleracea* L. (spinach) in late 12th-mid 13th century AD France," *Veget. Hist. Archaeobot.* 23(2):153-165, 2014.
"Corresponding." Merriam-Webster.com. 2017. https://www.merriam-webster.com (Mar. 5, 2017).
Yang et al., "SpinachDB: A Well-Characterized Genomic Database for Gene Family Classification and SNP Information of Spinach," *PLoS One* 11(5):e0152706, 2016.
Affidavit of Alistair David Curson, regarding New Zealand Patent Application No. 630710, dated Dec. 18, 2018.
Affidavit of Daniel Joachim Peter Engelmoer, regarding New Zealand Patent Application No. 630710, dated Dec. 12, 2018.
Affidavit of Robert James Henry, regarding New Zealand Patent Application No. 630710, dated Dec. 14, 2018.
Second Amended Statement of Case regarding New Zealand Patent No. 630710, dated Apr. 23, 2019.
Affidavit of Jessica Casbolt, regarding New Zealand Patent No. 630710, dated Apr. 16, 2019.
Affidavit of Johanna Maria Elisabeth Jacobs, regarding New Zealand Patent No. 630710, dated May 7, 2019.
Second Affidavit of John Charles Phillips, regarding New Zealand Patent No. 630710, dated Apr. 19, 2019.
Second Affidavit of Anneke Rijpkema, regarding New Zealand Patent No. 630710, dated Apr. 18, 2019.
Affidavit of Anneke Rijpkema, regarding New Zealand Patent Application No. 630710, dated Oct. 6, 2017.
Affidavit of John Charles Phillips, regarding New Zealand Patent Application No. 630710, dated Dec. 4, 2017.
Affidavit of Johanna Maria Elisabeth Jacobs, regarding New Zealand Patent Application No. 630710, dated Dec. 18, 2017.
Affidavit of Pieter Egelmeers, regarding New Zealand Patent Application No. 630710, dated Oct. 11, 2017.
Affidavit of Joel Kniskern in Reply to Opponent's Evidence, regarding New Zealand Patent Application No. 630710, dated Oct. 16, 2018.
U.S. Appl. No. 16/680,292, filed Nov. 11, 2019, Brugmans et al.
Examination Report dated Sep. 26, 2014 in New Zealand Application No. 630710.
Examination Report dated Jul. 13, 2015 in New Zealand Application No. 630710.
Official Gazette of the Community Plant Variety Office; Issue #6; accessed from www.cpvo.europa.eu; European Union Publications Office, 2013.
Kik et al., "Spinach, Armenia and Azerbaijan, 2011" Retrieved on Dec. 5, 2018. Available at <https://missions.cgn.wur.nl/NTC/NTC.htm>.

(56) References Cited

OTHER PUBLICATIONS

Amended Notice of Opposition to Grant of Patent and Statement of Case regarding New Zealand Patent No. 630710, dated Sep. 30, 2016.
Counterstatement regarding New Zealand Patent No. 630710, dated Dec. 5, 2016.
Amended Notice of Opposition to Grant of Patent and Amended Statement of Case regarding New Zealand Patent No. 630710, dated Oct. 9, 2017.
Amended Counterstatement regarding New Zealand Patent No. 630710, dated Nov. 10, 2017.
Further Amended Counterstatement regarding New Zealand Patent No. 630710, dated Nov. 14, 2017.
Feng et al., "Identification of New Races and Deviating Strains of the Spinach Downy Mildew Pathogen *Peronospora farinosa* f. sp. *spinaciae*," *Plant Disease* 98:145-152, 2014.
Wisley Trials, 1991, Spinach, Autumn Sown, available at http://apps.rhs.org.uk/planttrials/TrialReports/Spinach%20Autumn%20sown%201991.pdf, cited Sep. 30, 2016.
Nunhems USA, "Spinach Fresh Market Hybrids," available at http://nunhemsusa.com/www/NunhemsInternet.nsf/id/US_EN_Spinach_Fresh_Market, accessed Sep. 30, 2016.
Rijk Zwaan, "Dromedary RZ F1 ," Products & Services, dated May 20, 2016.
Rijk Zwaan, "Antelope RZ F1 ," Products & Services, dated May 20, 2016.
Rijk Zwaan, "Gazelle RZ F1," Products & Services, dated May 20, 2016.
Variety Description regarding SPN494 (Pigeon), available at <<https://www.naktuinbouw.nl/file/6268/download?token=r9E--zrv>>, cited in the Amended Notice of Opposition to Grant of Patent and Statement of Case regarding New Zealand Patent No. 630710, dated Sep. 30, 2016.
Rijk Zwaan, "Pigeon RZ F1," Products & Services, dated May 20, 2016.
Correll et al., "Denomination of Pfs: 15, a new race of downy mildew in spinach," *Plantum*, Sep. 2, 2014.
"Lettuce & Spinach" *Terranova Seeds*, Nov. 2012.
Variety Description regarding SPN496 (Racoon), available at <<https://www.naktuinbouw.nl/sites/default/files/variety/Groente/SPN-Racoon-NL-2010.pdf>>, cited in the Amended Notice of Opposition to Grant of Patent and Amended Statement of Case regarding New Zealand Patent No. 630710, dated Oct. 9, 2017.
Rijk Zwaan, "Racoon RZ F1 (51-317)," available at <<https://www.rijkzwaanusa.com/find-your-variety/spinach/racoon-rz>>, dated Jul. 21, 2017.
Document 21 Plantum Press release Denomination of a new race of downy mildew in spinach Published Sep. 2, 2014.†
Document 4 Wisley trials 1991Spinach autumn sown.†
Document 1 Feng C et al 2014 Identification of New Races and Deviating Strains of the Spinach Downy Mildew Pathogen Peronospora farinosa Spinaciae Plant Disease 981 145-152.†
Document 12 Nunhems Vegetable Seeds—USA and Canada—Crops Spinach Fresh Market Scorpius.†
Document 16 Rijk Zwaan Products & Services Dromedary RZ F1.†
Document 17 Rijk Zwaan Products & Services Antelope RZ F1.†
Document 18 RijkZwaan Products & Services Gazelle RZ F1.†
Document 19 Variety Description Pigeon—Published Feb. 25, 2011.†
Document 20 RijkZwaan Products & Services Pigeon RZ F1.†

\* cited by examiner
† cited by third party

Single hybrid A:  P1 (A/A)   x   P2(C/C)

F1(A/C)

Single hybrid B:  P1 (Vt/Vt) x   P2(C/C)

F1(Vt/C)

Single hybrid C:  P1 (A/A)   x   P2(Vt/Vt)

F1(A/Vt)

Three-way hybrid 1: P1 (A/A) x P1(Vt/Vt)   P2(C/C)

P1(A/Vt)  x   P2(C/C)

F1 (A/C) and F1 (Vt/C)

Three-way hybrid 2: P1 (A/A) x P1(C/C)    P2(Vt/Vt)

P1(A/C)   x   P2(Vt/Vt)

F1 (A/Vt) and F1 (C/Vt)

Three-way hybrid 3: P1 (C/C) x P1(Vt/Vt)   P2(A/A)

P1(C/Vt)  x   P2(A/A)

F1 (C/A) and F1 (Vt/A)

FIG. 3

SF63815 (SDA00431)
>C (SEQ ID NO:1)    25413 TAGGGGTAATTAACCAAATTGGTATTAAATTATACCCATTTGCCCTGTTGGTGTAAAGGTCGATGGATGAGTATAAATATTACTCTCTCCGTC 25504
>A (SEQ ID NO:2)    25413 TGGGGCTAATTAACCAGATTGGTATTAAATTAACTATACCCATTTGCCACGTTGGTGTAAAGGTCGATGGATG:G:::::::::::::::::: 25504
>VT (SEQ ID NO:3)   25413 TAGGGGTAATTAACCAGATTGGTATTAAATTATACCCATTTGCCACGTTGGTGTAAAGGTCGATGGATGAGTATAAATATTACTCTCTCTGTC 25504

SF59002 (SDA00548)
>C (SEQ ID NO:4)    4739 AAGGTTTGATGCTGCAAGAGAAAAGTAGATTTAGAAACGGGTAAACAGTGAAAAAAAGATGGAATATTACTCATACTATAACATTTGTTTCAAGGAAACCAT 4838
>A (SEQ ID NO:5)    4739 AAGGTTTGACGCTGCAAGACAAAGGTAGATTTAGAAACGGGTAGATTTAGAAACGGGTCAACAGTAAAAAAAAGATGGAA:::TTACTCATACTATAACATTTGTTTCAAGGAAACCAT 4838
>VT (SEQ ID NO:6)   4739 AAGGTTTGACGCTGCAAGACAAAGGTAGATTTAGAAACGGGTCAACAGTAAAAAAAAGATGGAA:::TTACTCATACTATAACATTTGTTTCAAGGAAACCAT 4838

SF59002 (SDA00556)
>A (SEQ ID NO:7)    280 AAGTTATGTTAGGCTTGGGAATGGAAGGTTATTCACTGGGACGTCTATTTATAAAGGGAGGGTGAATTTGTCCGTCAAGAAGTGTACCCGATTGTGTATA 380
>VT (SEQ ID NO:8)   280 AAGTTATGTTAGGCTTGGGAATGGAAGGTTATTCACTGGGACGTCTATTTATAAAGGGAGGAGTGAATTTGTCCGTCAAGAAGTGTACCCGATTGTGTATA 380

SF95487 (SDA00550)
>C (SEQ ID NO:9)    9520 TAATATCAATATTTTTATATAAACCATTTAATAAATTATTCCCTTCGTCCCTTAATATTCGACCCGATTTGACTTTTTGCACT:GTTACATAATTCAAT 9620
>A (SEQ ID NO:10)   9520 TAATATCAATATTTTTATATAAACCATTTAATAAATTACTCCCTCCGTCTCTTAATACTCGACTCGCTTGACTTTTTGCACTATTTACATAATTCAAT 9620
>VT (SEQ ID NO:11)  9520 TAATATCAATATTTTTATATAAACCATTTAATAAATTACTCCCTCCGTCCGTCCGCTTGACTTTTTGCACTATTTACATAATTCAAT 9620

SF90906 (SDA00543)
>C (SEQ ID NO:12)   38172 TTGAATGAGAACTTTGATTTTAGAAAGGAAGATAACAACAAGTTTTCTGTTTTCTGTTTTCACAAAATTAAAAAATCAAAATATAAAAATCACAAAAAGTAA:TTTTCAG 38173
>A (SEQ ID NO:13)   38172 TTGAATGAGAACTTTGATTTTAGAAAGGAAGAAGAACAACAACAAGTTTTCTGTTTTCTGTTTTTACAAAATTAAAAAATCAAAATATAAAAATCACGAAAAGTAATTTTTCAG 38173
>VT (SEQ ID NO:14)  38172 TTGAATGAGAACTTTGATTTTAGAAAGGAAGAACAACAACAACAAGTTTTCTGTTTTCTGTTTTTCACAAAATT:AAAAATCAAAATATAAAAATCACGAAAAGTAA:TTTTC::: 38173

FIG. 3 (Continued)

SF90906 (SDA00543)
>C (SEQ ID NO:15)   38012 AACTAACACTACTAAAAAATGATGTGATTTTTTATTTTATTTTTTCATCTAAAAAAGAAAAGACAAGAAACCCCAATCACACCGTAACCCTTAAAAG 38112
>A (SEQ ID NO:16)   38012 AACTAACACTACTAAAAAATGATGTGATTTTTTATTTTATTTTTTCATCTAAAAAAGAAAAGACAAGAAACCCCAATCACACCGTAACCCTTAAAAG 38112
>VT (SEQ ID NO:17)  38012 AACTAACACTACTAAAAAATGATGTGATTTTTTATTTTATTTTTTCATCTAAGAAAAGAAAAGACAAGAAACCCCAATCACACCGTAACCCTTAAAAG 38112

SF34732 (SDA00375)
>C (SEQ ID NO:18)   29522 GGCTCAATGTCATGTTTTCTACAAAATGGCACCCATAACTCGGCAAAGCTAGTGCCTCAGCCATTGCCTCGAAAGTTAGGAGAGCGCCGCCATCATCGGA 29622
>A (SEQ ID NO:19)   29522 GGCTCAATGTCATGTTTTCTACAAAATGGCACCCATAACTCGGCAAAGCTAGTGCCTCAGCCATTGCCTCGAAAGTTAGGAGAGCGCCGCCATCATCGGA 29622
>VT (SEQ ID NO:20)  29522 GGCTCAATGTCATGTTTTCTACAAAATGGCACCCATAACTCGGCAAAGCTAGTGCCTCAGCCATTGCCTCGAAAGTTAGGAGAGCGCCGCCATCATCGGA 29622

SF34732 (SDA00374)
>C (SEQ ID NO:21)   30525 GCAATCGTTACATATTGTAAATCTGCATATAATAAAAATTATAAAAAAATAAAATTGATATTCTAAAACATTTTAATTGTCGCAACTTACGAACCTTTATCAT 30625
>A (SEQ ID NO:22)   30525 GCAATCGTTACATATTGTAAATCTGCATATAATAAAAATTGTAAAAAAATAAAATTGATATTCTAAAACATTTTAATTGTCGCAACTTACGAACCTTTATCAT 30600
>VT (SEQ ID NO:23)  30525 GCAATCGTTACATATTGTAAATCTGCATATAATAAAAATTATAAAAAAATAAAATTGATATTCTAAAACATTTTAATTGTGGCAACTTACGAACCTTTATCAT 30625

SF62749 (SEQ ID NO:24)
>C, A AND Vt:
AAAATGCAACACAATCTATCTTAACCTAATCATTAAGTTGAATAATCAACTATTAACCCAAAAATGACTGCTCTTATCATTAAGTTGAATAATCAGTAGATATTGCCTAGTGAACCATCAAACAAATTAAAAATGCAACACAAT
CTATCTTAACCTAATCATTAAGTTGAATAATCAACTATTAACCCGAAAAATGGCTGCTCTTTTAAACCCGTTCATCTTTCTCAAC

SF178637 (SEQ ID NO:25)
>C, A AND Vt:
AGAATCGTCCTGTTAATCGATCTAAACCCTCTTCTCCACCTCCAAAACCCTAAATCTACATCACTTCAATCCTCACTTCCGCCAAAATTCTCCTCTCATTCCCCCTCTTTCTTCTTTCCCTATCCTCCTCCTTCAAGCTCTTCTCT
CTTCTCTATCCTCCTCCTCAAATGTCATCCTCGCTCCCAACTTCCCAATTTCA

SEQUENCE LISTING

<160> NUMBER OF SEQ ID NOS: 25

<210> SEQ ID NO 1
<211> LENGTH: 93
<212> TYPE: DNA
<213> ORGANISM: Spinacia oleracea

<400> SEQUENCE: 1

```
tagggtaat taaccaaatt ggtattaaat tatacccatt tgccctgttg gtgtaaaggt    60
cgatggatga gtataaatat tactctctcc gtc                                93
```

<210> SEQ ID NO 2
<211> LENGTH: 70
<212> TYPE: DNA
<213> ORGANISM: Spinacia oleracea

<400> SEQUENCE: 2

```
tggggctaat taaccagatt ggtattaact tatacccatt tgccacgttg gtgtaaaggt    60
cgatggatgg                                                          70
```

<210> SEQ ID NO 3

```
<211> LENGTH: 93
<212> TYPE: DNA
<213> ORGANISM: Spinacia oleracea

<400> SEQUENCE: 3 tagggtaat taaccagatt ggtattaaat tatacccatt tgccacgttg gtgtaaaggt      60
cgatggatga gtataaatat tactctctct gtc                                  93

<210> SEQ ID NO 4
<211> LENGTH: 102
<212> TYPE: DNA
<213> ORGANISM: Spinacia oleracea

<400> SEQUENCE: 4
aaggtttgat gctgcaagag aaaagtagat ttagaaacgg gtaaacagtg aaaaaaagat     60
ggaatattac tcatactata acatttgttt caaggaaacc at                       102

<210> SEQ ID NO 5
<211> LENGTH: 100
<212> TYPE: DNA
<213> ORGANISM: Spinacia oleracea

<400> SEQUENCE: 5
aaggtttgac gctgcaagac aaaggtagat ttagaaacgg gtcaacagta aaaaaaagat     60
ggaattactc atactataac atttgtttca aggaaaccat                          100

<210> SEQ ID NO 6
<211> LENGTH: 100
<212> TYPE: DNA
<213> ORGANISM: Spinacia oleracea

<400> SEQUENCE: 6
aaggtttgac gctgcaagac aaaggtagat ttagaaacgg gtcaacagta aaaaaaagat     60
ggaattactc atactataac atttgtttca aggaaaccat                          100

<210> SEQ ID NO 7
<211> LENGTH: 101
<212> TYPE: DNA
<213> ORGANISM: Spinacia oleracea

<400> SEQUENCE: 7
aagttatgtt aggcttggga atggaaggtt attcactggg acgtctattt ataaagggag     60
ggtgaatttg tccgtcaaga agttgtaccc gattgtgtat a                        101

<210> SEQ ID NO 8
<211> LENGTH: 101
<212> TYPE: DNA
<213> ORGANISM: Spinacia oleracea

<400> SEQUENCE: 8
aagttatgtt aggcttggga atggaaggtt attcactggg acgtctattt ataaagggag     60
gatgaatttg tccgtcaaga agttgtaccc gattgtgtat a                        101

<210> SEQ ID NO 9
<211> LENGTH: 100
<212> TYPE: DNA
<213> ORGANISM: Spinacia oleracea

<400> SEQUENCE: 9
taatatcaat attttttata taaaccattt taataaatta ttcccttcgt cccttaatat     60
```

```
tcgacccgat ttgactttt  gcactgttac ataattcaat                    100

<210> SEQ ID NO 10
<211> LENGTH: 101
<212> TYPE: DNA
<213> ORGANISM: Spinacia oleracea

<400> SEQUENCE: 10
taatatcaat attttttata aaaccattt  taataaatta ctccctccgt ctcttaatac    60
tcgactcgct ttgactttt  gcactattta cataattcaa t                      101

<210> SEQ ID NO 11
<211> LENGTH: 101
<212> TYPE: DNA
<213> ORGANISM: Spinacia oleracea

<400> SEQUENCE: 11
taatatcaat attttttata aaaccattt  taataaatta ctccctccgt ctcttaatac    60
tcgactcgct ttgactttt  gcactattta cataattcaa t                      101

<210> SEQ ID NO 12
<211> LENGTH: 103
<212> TYPE: DNA
<213> ORGANISM: Spinacia oleracea

<400> SEQUENCE: 12
ttgaatgaga actttgattt tagaaaggaa gataacaaca agttttctgt ttttcacaaa    60
attaaaaaat caaatataa  aaatcacaaa aagtaatttt cag                   103

<210> SEQ ID NO 13
<211> LENGTH: 104
<212> TYPE: DNA
<213> ORGANISM: Spinacia oleracea

<400> SEQUENCE: 13
ttgaatgaga actttgattt tagaaaggaa gacaacaaca agttttctgt tttttacaaa    60
attaaaaaat caaatataa  aaatcacgaa aagtaatttt tcag                  104

<210> SEQ ID NO 14
<211> LENGTH: 100
<212> TYPE: DNA
<213> ORGANISM: Spinacia oleracea

<400> SEQUENCE: 14
ttgaatgaga actttgattt tagaaaggaa gacaacaaca agttttctgt ttttcacaaa    60
attaaaaatc aaatataaa  aatcacgaaa agtaattttc                       100

<210> SEQ ID NO 15
<211> LENGTH: 101
<212> TYPE: DNA
<213> ORGANISM: Spinacia oleracea

<400> SEQUENCE: 15
aactaacact actaaaaaat gatgtgattt tttatttat  tttttcatct aaaaaaagaa    60
aagaacaaga aaccccaat  cacaccgtaa cccttaaaaa g                     101

<210> SEQ ID NO 16
<211> LENGTH: 101
<212> TYPE: DNA
```

<213> ORGANISM: Spinacia oleracea

<400> SEQUENCE: 16
aactaacact actaaaaaat gatgtgattt tttattttat tttttcatct aagaaaagaa    60
aagaacaaga aacccccaat cacaccgtaa cccttaaaaa g                        101

<210> SEQ ID NO 17
<211> LENGTH: 101
<212> TYPE: DNA
<213> ORGANISM: Spinacia oleracea

<400> SEQUENCE: 17
aactaacact actaaaaaat gatgtgattt tttattttat tttttcatct aagaaaagaa    60
aagaacaaga aacccccaat cacaccgtaa cccttaaaaa g                        101

<210> SEQ ID NO 18
<211> LENGTH: 101
<212> TYPE: DNA
<213> ORGANISM: Spinacia oleracea

<400> SEQUENCE: 18
ggctcaatgt catgttttct acaaaatggc acccataact cggcaaagct agctgcctca    60
gccattgcct cgaaagttag gagagcgccg ccatcatcgg a                        101

<210> SEQ ID NO 19
<211> LENGTH: 101
<212> TYPE: DNA
<213> ORGANISM: Spinacia oleracea

<400> SEQUENCE: 19
ggctcaatgt catgttttct acaaaatggc acccataact cggcaaagct agctgcctca    60
gccattgcct cgaaagttag gagagcgccg ccatcatcgg a                        101

<210> SEQ ID NO 20
<211> LENGTH: 101
<212> TYPE: DNA
<213> ORGANISM: Spinacia oleracea

<400> SEQUENCE: 20
ggctcaatgt catgttttct acaaaatggc acccataact cggcaaagct agctgcttca    60
gccattgcct cgaaagttag gagagcgccg ccatcatcgg a                        101

<210> SEQ ID NO 21
<211> LENGTH: 102
<212> TYPE: DNA
<213> ORGANISM: Spinacia oleracea

<400> SEQUENCE: 21
gcaatcgtta catattgtaa atctgcatat aataaaaatt ataaaaaaat aaattgatat    60
tctaaaacat tttaattgtc gcaacttacg aacctttatc at                       102

<210> SEQ ID NO 22
<211> LENGTH: 102
<212> TYPE: DNA
<213> ORGANISM: Spinacia oleracea

<400> SEQUENCE: 22
gcaatcgtta catattgtaa atctgcatat aataaaaatt gtaaaaaat aaattgatat     60 tctaaaacat tttaattgtc gcaacttacg aacctttatc at                       102

```
<210> SEQ ID NO 23
<211> LENGTH: 102
<212> TYPE: DNA
<213> ORGANISM: Spinacia oleracea

<400> SEQUENCE: 23
gcaatcgtta catattgtaa atctgcatat aataaaaatt ataaaaaaat aaattgatat      60
tctaaaacat tttaattgtg gcaacttacg aacctttatc at                       102

<210> SEQ ID NO 24
<211> LENGTH: 239
<212> TYPE: DNA
<213> ORGANISM: Spinacia oleracea

<400> SEQUENCE: 24
aaaatgcaac acaatctatc ttaacctaat cattaagttg aataatcaac tattaaccca     60
aaaaatgact gctcttatca ttaagttgaa taatcagtag atattgccta gtgaaccatc    120
aaacaaatta aaaatgcaac acaatctatc ttaacctaat cattaagttg aataatcaac    180
tattaacccg aaaaatggct gctctttaa  acctttgaaa cccgttcatc tttctcaac     239

<210> SEQ ID NO 25
<211> LENGTH: 198
<212> TYPE: DNA
<213> ORGANISM: Spinacia oleracea

<400> SEQUENCE: 25
agaatcgtcc tgttaatcga tctaaaccct cttctccacc tccaaaaccc taaatcttac     60
atcacttcaa tcctcacttc cgccaaaatt ctcctctcat ttcccctct ttctctttcc    120 ctatcctcct tcaagctctt cttctcttct ctatctcctc tcaaatcgtc atcctcgctc    180
cccaacttcc caatttca                                                  198
```

US 10,927,386 B2

COMPOSITIONS AND METHODS FOR PERONOSPORA RESISTANCE IN SPINACH

CROSS REFERENCE TO RELATED APPLICATIONS

This application claims the benefit of U.S. Provisional Application No. 61/945,675, filed Feb. 27, 2014, herein incorporated by reference in its entirety.

INCORPORATION OF SEQUENCE LISTING

The sequence listing that is contained in the file named "SEMB015US_ST25.txt," which is 6.2 kilobytes as measured in Microsoft Windows operating system and was created on Feb. 25, 2015, is filed electronically herewith and incorporated herein by reference.

FIELD OF THE INVENTION

The invention relates to the field of plant breeding and, more specifically, to methods and compositions for producing spinach plants with resistance to downy mildew.

BACKGROUND OF THE INVENTION

Downy mildew, caused by the plant pathogen *Peronospora farinosa f.* sp. *Spinaciae* (Pfs), is an economically important disease of spinach worldwide, particularly for *Spinacia oleracea*, the most commonly cultivated spinach species. Currently, fourteen races of the downy mildew (DM)-causing pathogen are officially recognized, although new isolates are currently being discovered and named each year. To date, it has been believed that resistance to DM in spinach was incomplete and race-specific. The ability of new strains of the pathogen to overcome resistance in spinach plants therefore makes the development of spinach varieties with effective levels of resistance to *Peronospora farinosa f.* sp. *spinaciae* challenging and increasingly important.

SUMMARY OF THE INVENTION

In one aspect, the invention provides a *Spinacia oleracea* spinach plant comprising in its genome allele A, as described herein. In another aspect, the invention provides a *Spinacia oleracea* spinach plant comprising in its genome a heterozygous combination of alleles that confers broad-spectrum resistance to *Peronospora farinosa f.* sp. *Spinaciae*. In an embodiment, the broad-spectrum resistance comprises resistance to at least 10 races of *Peronospora farinosa f.* sp. *spinaciae* (Pfs). In another embodiment, the allele that confers broad-spectrum resistance is a combination of alleles which is selected from the group consisting of allele A, allele Vt, and allele C. In other embodiments, the combination of alleles comprises alleles A and C and the plant is resistant to at least *Peronospora farinosa f.* sp. *Spinaciae* races 7, 8, 10, 11, 12, 14, and isolate UA4712; the combination of alleles comprises alleles A and Vt, and the plant is resistant to at least *Peronospora farinosa f.* sp. *Spinaciae* races 7, 8, 10, 11, 12, 13, and 14; or the combination of alleles comprises alleles C and Vt, and the plant is resistant to at least *Peronospora farinosa f.* sp. *Spinaciae* races 7, 8, 10, 11, 12, 13, and isolate UA4712. In another embodiment, representative samples of seed comprising allele A, allele C, and allele Vt have been deposited under ATCC Accession No. PTA-120472, ATCC Accession No. PTA-12486, and ATCC Accession No. PTA-12041, respectively. In further embodiments, the allele A, allele C, and/or allele Vt is genetically linked to at least one sequence selected from the group SEQ ID NOs:1-25.

In another embodiment, a plant of the invention comprises an allele A, allele C, and/or allele Vt that shares a genetic source for said allele with seed deposited under ATCC Accession Nos. PTA-120472, ATCC Accession No. PTA-12486, or ATCC Accession No. PTA-12041. In other embodiments, a plant of the invention may be an inbred or a hybrid. In still further embodiments, the invention provides a seed that produces such a plant, or a plant part of such a plant. In another embodiment, the plant part is selected from the group consisting of an embryo, meristem, cotyledon, pollen, leaf, anther, root, pistil, flower, cell, and stalk. In a still further embodiment, the invention provides a food product comprising the harvested leaves of such a spinach plant.

In another aspect, the invention provides a *Spinacia oleracea* spinach plant comprising in its genome a heterozygous combination of alleles that confers broad-spectrum resistance to *Peronospora farinosa f.* sp. *Spinaciae*, wherein one allele confers recessive resistance to *Peronospora farinosa f.* sp. *Spinaciae* races 7 and 13. In one embodiment, the broad-spectrum resistance comprises resistance to at least 10 races of *Peronospora farinosa f.* sp. *spinaciae* (Pfs). In other embodiments, one allele is allele Vt and the other allele is allele C, one allele is allele A and the other is allele Vt; or one allele is allele A and the other is allele C.

In another aspect, the invention provides a method of producing a spinach plant with broad spectrum resistance to *Peronospora farinosa f.* sp. *Spinaciae* comprising: (a) crossing a first spinach plant comprising in its genome a first allele selected from the group consisting of A, Vt, and C, with a second spinach plant comprising in its genome a second allele selected from the group consisting of A, Vt, and C, to produce a population of hybrid progeny plants; and (b) selecting at least one hybrid progeny plant from said population that comprises a combination of said first allele and said second allele that confers broad-spectrum resistance to *Peronospora farinosa f.* sp. *Spinaciae*. In one embodiment, the method further comprises production of a population of hybrid plants. In other embodiments, the first spinach plant comprises allele A and the second spinach plant comprises allele C; or the first spinach plant comprises allele A and the second spinach plant comprises allele Vt; or the first spinach plant comprises allele C and the second spinach plant comprises allele Vt. In another embodiment, the invention provides a hybrid progeny plant produced by such a method. In still other embodiments, the first allele of the plant is allele A and the second allele is allele C; or the first allele is allele A and the second allele is allele Vt; or the first allele is allele C and the second allele is allele Vt.

In another aspect, the invention provides a method of introducing resistance to *Peronospora farinosa f.* sp. *Spinaciae* in a spinach plant comprising: (a) crossing a first spinach plant comprising in its genome a first allele selected from the group consisting of A, Vt, and C, with a second spinach plant comprising in its genome a second, distinct allele; (b) selecting at least one progeny plant that comprises said first allele for resistance to *Peronospora farinosa f.* sp. *Spinaciae* based on the presence in the genome of the plant of a sequence selected from SEQ ID NOs:1-25. In another embodiment, the method comprises detecting in the genome of said plant at least two polymorphic nucleic acid sequences selected from the group consisting of SEQ ID NOs:1-25, wherein the presence of the polymorphic nucleic acid sequences are indicative of the presence in the plant of at least two alleles conferring resistance to *Peronospora farinosa f.* sp. *Spinaciae* selected from of alleles A, Vt, and C.

In yet another aspect, the invention provides a spinach plant, cell or cell containing plant part comprising at least two polymorphic DNA sequences which are associated with different alleles from among alleles A, Vt, and C. In one embodiment, a spinach plant, cell or cell containing plant part are provided comprising at least two DNA sequences that are represented in different groups from among those designated (a), (b) and (c), said groups being made up as follows: (a) a DNA sequence comprising SEQ ID NO:2, SEQ ID NO:5, SEQ ID NO:7, SEQ ID NO:10, SEQ ID NO:13, SEQ ID NO:16, SEQ ID NO:19, or SEQ ID NO:22; (b) a DNA sequence comprising SEQ ID NO:1, SEQ ID NO:4, SEQ ID NO:9, SEQ ID NO:12, SEQ ID NO:15, SEQ ID NO:18, SEQ ID NO:21, or SEQ ID NO:22; and (c) a DNA sequence comprising SEQ ID NO:3, SEQ ID NO:6, SEQ ID NO:8, SEQ ID NO:11, SEQ ID NO:14, SEQ ID NO:17, SEQ ID NO:20, or SEQ ID NO:23. The invention also provides a DNA sequence selected from the group consisting of SEQ ID NOs:1-25.

BRIEF DESCRIPTION OF THE SEQUENCE LISTING

SEQ ID NO:1—DNA sequence corresponding to scaffold SF63815 and diagnostic for allele C.
SEQ ID NO:2—DNA sequence corresponding to scaffold SF63815 and diagnostic for allele A.
SEQ ID NO:3—DNA sequence corresponding to scaffold SF63815 and diagnostic for allele Vt.
SEQ ID NO:4—DNA sequence corresponding to scaffold SF59002 and diagnostic for allele C.
SEQ ID NO:5—DNA sequence corresponding to scaffold SF59002 and diagnostic for allele A.
SEQ ID NO:6—DNA sequence corresponding to scaffold SF59002 and diagnostic for allele Vt.
SEQ ID NO:7—DNA sequence corresponding to scaffold SF59002 and diagnostic for allele A.
SEQ ID NO:8—DNA sequence corresponding to scaffold SF59002 and diagnostic for allele Vt.
SEQ ID NO:9—DNA sequence corresponding to scaffold SF95487 and diagnostic for allele C.
SEQ ID NO:10—DNA sequence corresponding to scaffold SF95487 and diagnostic for allele A.
SEQ ID NO:11—DNA sequence corresponding to scaffold SF95487 and diagnostic for allele Vt.
SEQ ID NO:12—DNA sequence corresponding to scaffold SF90906 and diagnostic for allele C.
SEQ ID NO:13—DNA sequence corresponding to scaffold SF90906 and diagnostic for allele A.
SEQ ID NO:14—DNA sequence corresponding to scaffold SF90906 and diagnostic for allele Vt.
SEQ ID NO:15—DNA sequence corresponding to scaffold SF90906 and diagnostic for allele C.
SEQ ID NO:16—DNA sequence corresponding to scaffold SF90906 and diagnostic for allele A.
SEQ ID NO:17—DNA sequence corresponding to scaffold SF90906 and diagnostic for allele Vt.
SEQ ID NO:18—DNA sequence corresponding to scaffold SF34732 and diagnostic for allele C.
SEQ ID NO:19—DNA sequence corresponding to scaffold SF34732 and diagnostic for allele A.
SEQ ID NO:20—DNA sequence corresponding to scaffold SF34732 and diagnostic for allele Vt.
SEQ ID NO:21—DNA sequence corresponding to scaffold SF34732 and diagnostic for allele C.
SEQ ID NO:22—DNA sequence corresponding to scaffold SF34732 and diagnostic for allele A.
SEQ ID NO:23—DNA sequence corresponding to scaffold SF34732 and diagnostic for allele Vt.
SEQ ID NO:24—DNA sequence corresponding to alleles A, C, and Vt of scaffold SF62749.
SEQ ID NO:25—DNA sequence corresponding to alleles A, C, and Vt of scaffold SF178637.

BRIEF DESCRIPTION OF THE DRAWINGS

FIG. 3: Shows sequence alignments of scaffolds containing polymorphisms corresponding to alleles C, A, and Vt. Polymorphisms between alleles are underlined, and can be used to identify and/or diagnose the presence of downy mildew resistance alleles C, A, and/or Vt in spinach.

DETAILED DESCRIPTION OF THE INVENTION

Figure 1:
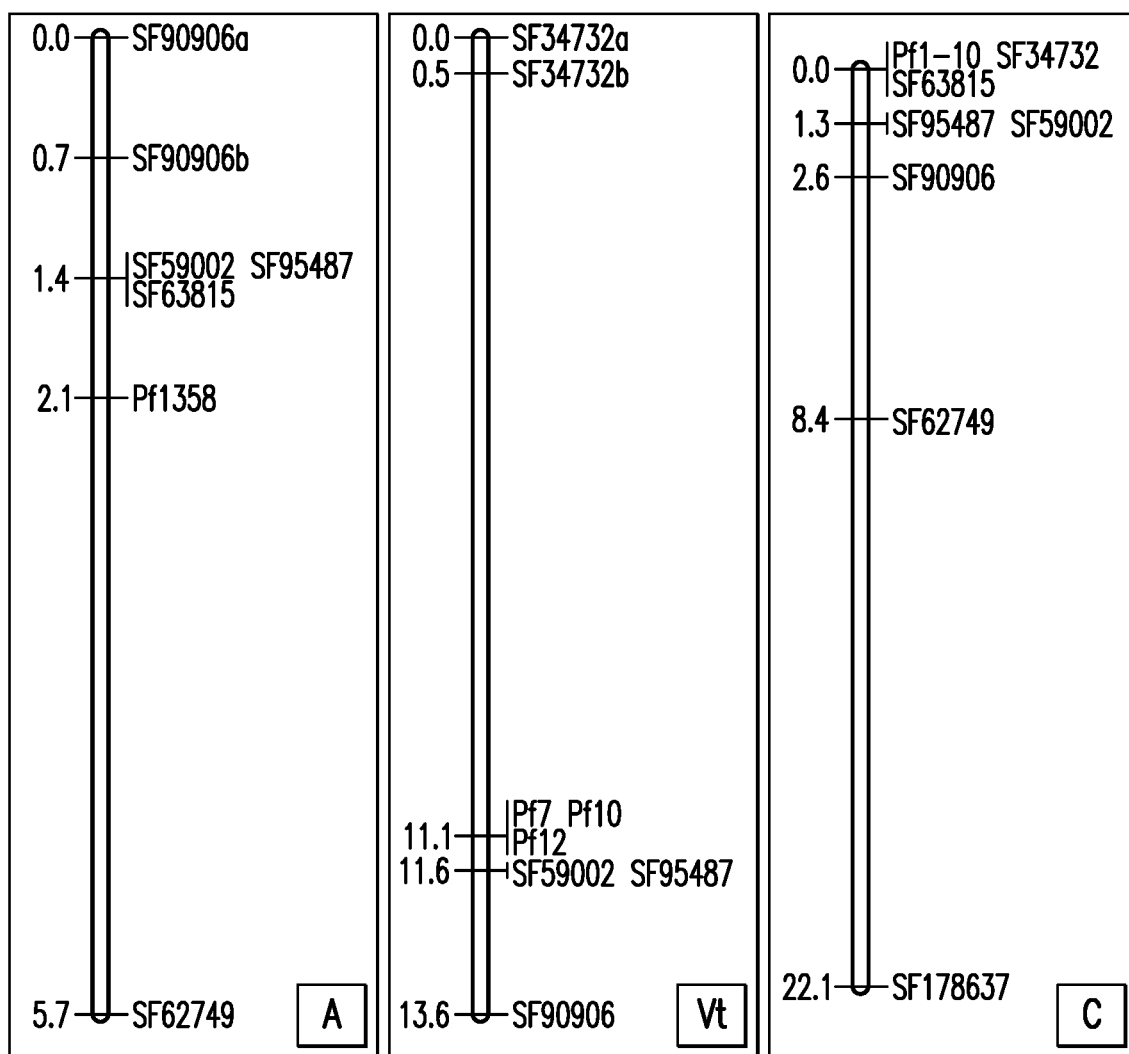
FIG. 1: Shows alleles A, Vt, and C, which represent three linkage groups assembled from genotypes and phenotypes collected for three mapping populations, as described in Example 3.

The present invention provides methods and compositions for development of spinach varieties with resistance to downy mildew (DM). The invention provides the identification of three distinct alleles from *Spinacia oleracea*, which have been named A, Vt, and C. These alleles can be used in various combinations to obtain spinach plants with a unique broad-spectrum resistance to DM.

The three alleles, designated A from spinach line SMBS011-1162M, C from SMB-66-1143M, and Vt from SSB-66-1131M, were identified in *Spinacia oleracea* and found to provide resistance to existing and emerging DM strains. Each allele was found to have resistance to a specific set of races and/or isolates. The alleles can be used in various combinations to make hybrids with desired DM resistance.

As shown in further detail herein below, allele C was found to confer resistance to races 1, 2, 3, 4, 5, 6, 7, 8, 10 and newly occurring Pfs isolate UA4712, which is the candidate strain for race 15. Allele A was found to confer resistance to *Peronospora farinosa* (Pfs) races 1, 3, 5, 7, 8, 11, 12, 13 and 14. The resistance to races 7 and 13, unlike most DM races, is inherited in a recessive manner. Allele Vt was found to confer resistance to races 1, 2, 3, 4, 5, 6, 7, 8, 10, 11, 12 and 13. These newly characterized alleles can be used in novel heterozygous combinations to obtain spinach plants with broad DM resistance. The spinach plants may be inbred plants and/or hybrid plants and can include various combinations of the alleles as described herein.

For example, in accordance with one embodiment of the invention, alleles C and Vt can be present in a spinach plant (i.e., a heterozygous spinach plant) and provide resistance to Pfs races 1-8, 10-13, and to newly occurring Pfs isolate UA4712. In another embodiment, alleles A and Vt can be present in a spinach plant and provide resistance to Pfs races 1-8 and 10-14. Allele Vt complements the recessive resistances from allele A. Similarly, when alleles A and C are present together in a spinach plant, the plant is resistant to Pfs races 1-8, 10-12, 14 and UA4712. The alleles can be utilized in any combination to provide desired resistance for a particular market or region. For example, a hybrid with alleles C and Vt exhibits resistance to all Pfs races except Pfs 14. Since Pfs race 14 does not occur in Europe, this hybrid would be fully resistant in that geography. As a further example, a hybrid with alleles A and Vt exhibits resistance to all Pfs races except isolate UA4712. New isolate UA4712 is found in limited locations, so this hybrid would be fully resistant in many areas.

In yet another embodiment, a three-way hybrid is contemplated that is resistant to all described DM races and isolate UA4712. In accordance with the invention, a spinach plant comprising one or two alleles described herein, including, but not limited to, A, C, and Vt, can be crossed with a second, distinct spinach plant comprising a second or third allele including, but not limited to, A, C, and Vt to produce a hybrid spinach plant comprising a beneficial set of alleles as described herein.

As further described herein, alleles can be introgressed into selected spinach varieties in any combination to provide a desired resistance to DM. In accordance with the invention, such alleles conferring resistance to DM may be introgressed into any desired genomic background of a specific spinach variety or cultivar. For example, a starting spinach plant containing a given DM resistance allele in accordance with the invention can be self-fertilized a sufficient number of generations to produce an inbred spinach variety that is homozygous for the allele conferring resistance to DM. Such an inbred plant may then be crossed with another spinach plant that comprises a distinct DM resistance allele to consistently produce spinach inbreds and/or hybrids that comprise a combination of alleles conferring a desirable resistance to DM as described herein. A spinach plant exhibiting resistance to DM according to the invention may further be crossed to other spinach plants and selections carried out according to the invention to obtain new DM-resistant spinach inbreds and hybrids with any desired combination of alleles described herein.

Although other alleles conferring resistance to certain races of DM have previously been identified in spinach, such alleles have conferred resistance only to a subset of races of *Peronospora farinose* (Pfs), even in a hybrid combination. Non-host resistance to DM may also be found in wild relatives of spinach, such as *Spinacia turkestanica* and *Spinacia tetrandra*. However, genes from wild relatives often result in negative drag for commercial characteristics including yield and quality. The unfavorable alleles found in the wild relatives are often introduced into the elite germplasm together with DM resistance alleles. The present invention describes novel *S. oleracea* resistance sources, alleles, and markers that provide race-specific and broad-spectrum DM resistance.

In one embodiment of the invention, alleles A, C, and Vt, conferring resistance to DM may be defined as being on spinach linkage group 6 by common markers in sequence scaffolds SF34732 and SF63815 on the distal position and SF59002, SF95487, and SF90906 on the proximal position. Nucleotide sequences associated with and diagnostic for the resistance alleles are provided in SEQ ID NOs:1-25. Polymorphisms between alleles A, C, and Vt are shown in FIG. 3. In other embodiments, alleles providing broad-spectrum resistance to DM may be defined as from, or sharing, a genetic source selected from accessions SMBS011-1162M, SMB-66-1143M, and SSB-66-1131M, representative deposits of seed of which were made with the ATCC under accession numbers PTA-120472, PTA-12486, and PTA-12041, respectively.

The invention further provides methods of producing spinach plants with broad-spectrum resistance to DM, as well as spinach plants and parts thereof made by such methods. In one embodiment, nucleic acid sequences or genomic markers may be used to identify alleles according to the present invention. These nucleic acid sequences may be used in the identification of polymorphisms or markers genetically linked in a spinach genome to the DM-resistance conferring alleles in accordance with the invention. The invention also provides food products derived from such plants and their method of production.

Genetic markers in linkage disequilibrium with DM-resistance alleles of the present invention may permit efficient introduction of DM-resistance into essentially any spinach genome. This also results in significant economization by permitting substitution of costly, time-intensive, and potentially unreliable phenotypic assays. Further, breeding programs can be designed to explicitly drive the frequency of specific favorable phenotypes by targeting particular genotypes. Fidelity of these associations may be monitored continuously to ensure maintained predictive ability and, therefore, informed breeding decisions.

In accordance with the invention, one of skill in the art may identify a candidate germplasm source possessing a desirable DM-resistant phenotype, such as from an accession described herein. One embodiment of the invention comprises using the materials and methods of the invention to obtain an allele conferring broad-spectrum resistance to DM from any additional spinach accessions. Using the information set forth herein, including, but not limited to, a sequence scaffold from spinach chromosome 6, DM resistance can be introgressed into any other spinach varieties.

The development of spinach varieties in a spinach breeding program requires, in general, the development of homozygous inbred lines, the crossing of these lines, and the evaluation of the resulting hybrid plants. Spinach breeding programs combine the genetic backgrounds from two or more inbred lines or various other germplasm sources into breeding populations from which new inbred lines are developed by selfing and selection of desired phenotypes. Hybrids also can be used as a source of plant breeding material or as source populations from which to develop or derive new spinach lines. Plant breeding techniques known in the art and used in a spinach breeding program include, but are not limited to, recurrent selection, backcrossing, double haploids, pedigree breeding, genetic marker enhanced selection, and transformation. Often a combination of these techniques is used. Thus, inbred lines derived from hybrids can be developed using plant breeding techniques as described above. New inbred lines can be crossed with other inbred lines and the hybrids from these crosses are evaluated to determine which of those have commercial potential.

The techniques of the present invention may be used to identify desirable disease-resistant phenotypes by identifying genetic markers genetically linked to an allele or locus conferring such a phenotype. In accordance with the invention, one of skill in the art may develop molecular marker assays based on, for example, SNPs and/or Indels in the spinach genome. In an embodiment, molecular marker assays useful to identify DM-resistant spinach plants according to the invention may be designed based on a sequence scaffold from spinach chromosome 6. Such techniques may also involve phenotypic assays to identify desired plants either alone or in combination with genetic assays, thereby also identifying a marker genotype associated with the trait that may be used for production of new varieties with the methods described herein.

The invention provides for the production of cultivated spinach plants comprising a combination of alleles conferring resistance to DM. Successful spinach production depends on attention to various horticultural practices. These include soil management with special attention to proper fertilization, crop establishment with appropriate spacing, weed control, and the introduction of bees or other insects for pollination, irrigation, and pest management.

Spinach crops can be established from seed or from transplants. Transplanting can result in an earlier crop compared to a crop produced from direct seeding. Transplanting helps achieve complete plant stands rapidly, especially where higher seed costs, as with triploid seeds, make direct-seeding risky.

Development of Spinach Plants with Resistance to Downy Mildew

The present disclosure identifies alleles from cultivated spinach and combinations thereof conferring broad-spectrum resistance to DM, as well as sequence scaffolds from spinach chromosome 6 that can be used for the tracking and introgression of the loci into desirable germplasm, such as by marker-assisted selection and/or marker-assisted backcrossing.

The invention provides for the tracking and introduction of any such alleles and/or any combination of such alleles with other resistance loci into a given genetic background. One of ordinary skill will understand that resistance to DM conferred by alleles described herein may be introgressed from one genotype to another via marker-assisted selection. Accordingly, a germplasm source can be selected that has resistance to DM. Using these alleles, a breeder may select a spinach plant with resistance to DM, or track such a phenotype during breeding using marker-assisted selection for the region described herein. According to the invention, screens with flanking markers may be sufficient to select progeny carrying desired DM resistance in pedigrees that segregate for a single resistance allele. One of skill in the art will also understand that markers can be complemented by phenotypic screens, for example with differential races showing a compatible interaction with one allele and an incompatible interaction with another, to select for individuals with desired resistance in populations segregating for two or more haplotypes.

Development of Spinach Hybrids with Resistance to Downy Mildew

As described herein, spinach plants in accordance with the present invention may comprise any heterozygous combinations of allele C, allele A, and allele Vt to confer broad DM resistance. For example, in one embodiment, alleles C and Vt can be present in a heterozygous spinach plant and confer resistance to Pfs races 1-8, 10-13, and to newly occurring Pfs isolate UA4712. In other embodiments, alleles A and Vt can be present in a spinach plant and confer resistance to Pfs races 1-8 and 10-14, or alleles A and C can be present together in a spinach plant and confer resistance to Pfs races 1-8, 10-12, 14 and UA4712. Also in accordance with the present invention is a three-way hybrid that is resistant to all described DM races and isolate UA4712. Such a spinach plant comprising one or two alleles as described herein may be crossed with a second, distinct spinach plant comprising a second or third allele as described herein to produce a hybrid spinach plant comprising a beneficial set of alleles as described herein.

The process of introgressing a novel resistance gene into acceptable commercial types can be a difficult process and may be complicated by factors such as linkage drag, epistasis, and low heritability. The heritability of a trait is the proportion of the phenotypic variation attributed to the genetic variance, which varies between 0 and 1.0. Thus, a trait with heritability near 1.0 is not greatly affected by the environment. Those skilled in the art recognize the importance of creating commercial lines with horticultural traits having high heritability because these cultivars will allow growers to produce a crop with uniform market specifications.

One of ordinary skill will understand that the resistance alleles provided herein can be combined for improved resistance, particularly in fields where mixed populations of DM races may occur. According to the invention, the alleles described herein may be introgressed into parents of a hybrid via marker-assisted and/or phenotypic selection. Breeders may select alleles that mutually complement race-specificity to achieve broad resistance to DM. The described resistance donors are crossed to inbreds with demonstrated combining ability. The F1 resulting from each initial cross is then backcrossed with the recipient genotype, i.e. with the recurrent parent. According to the invention, individuals carrying the resistance in the heterozygous phase are selected using marker-assisted and/or phenotypic selection. This backcross and selection step is repeated, for example, three times. Individuals carrying the desired resistance allele are then self-pollinated, for example, for two generations through single seed descent. A breeder may recover inbred spinach plants carrying the desired resistance allele from the progeny of each pedigree, introduced into the same genetic background as respective recurrent parents, preferably at least 95%, 96%, 97%, 98%, or 99% identical. Commercial, resistant cultivars are generated by crossing parental lines, each with a complementary resistance allele, thereby creating hybrids with superior resistance.

According to the invention, multiple resistance donors may be individually crossed to the same recipient genotype. Following the backcross and selection steps described above, an inbred spinach plant carrying a distinct resistance allele may be obtained that has been introduced into the same genetic background as the recurrent parent, preferably at least 95%, 96%, 97%, 98%, or 99% identical. One of skill in the art will understand that different resistance alleles may be maintained in the same, fixed genetic background, i.e. in near-isogenic lines. The steps to create inbreds that are near-isogenic for resistance alleles can be applied to both inbred parents of any hybrid. According to the invention, breeders may create three-way hybrids by crossing two near-isogenic lines derived from one parental line to generate an F1 seed parent. The F1 seed parent is crossed with the third parent carrying the complementary resistance allele. The resulting three-way hybrid is uniform, except for a complementary combination of DM resistance alleles. Hybrid plants consistently share the same genetic background as the recurrent parent, preferably at least 95%, 96%, 97%, 98%, or 99% identical, and carry various combinations of resistance alleles. The alleles provided herein allow for the consistent production of commercial varieties with broad DM resistance. Furthermore, the present invention provides alleles that can be used in different combinations to provide spinach plants for each area and/or region with distinct DM populations. In addition, a single variety can be obtained with a mix of resistance alleles to reduce pathogen pressure when resistance-breaking races or newly emerging isolates exist.

Genomic Region, Polymorphic Nucleic Acids, and Alleles Associated with DM Resistance Applicants have discovered three alleles from cultivated spinach, *S. oleracea*, that when present together in particular combinations in a hybrid (heterozygous) spinach plant, confer broad-spectrum resistance to DM. Using the methods outlined herein, these alleles were found to be located on spinach chromosome 6 in a locus that may be defined by sequence scaffolds SF34732 and SF63815 on the distal position and SF59002, SF95487, and SF90906 on the proximal position, or sequences at least 95% identical thereto, including sequences at least 96%, 97%, 98%, 99%, or 100% identical thereto, as one of skill in the art would understand that polymorphisms may exist in such regions in different populations. Polymorphisms that may be used to identify or diagnose the presence of resistance alleles C, A, and/or Vt are shown in FIG. 3. Examples of such nucleotide sequences are provided in SEQ ID NOs:1-25. These sequences may be used in accordance with the invention to identify or diagnose the presence or identity of a particular allele in a plant and thus identify plants that carry resistance to DM. One of skill in the art will further appreciate that many genetic markers can be located throughout the *S. oleracea* genome, and markers may be developed from SNPs and/or Indels in flanking sequences of the sequences described herein and in other fragments located throughout the *S. oleracea* genome. Such markers are useful in identifying the presence or absence of a resistance allele in accordance with the invention. Examples of markers in the spinach genome are described in, for example, Khattak et al. (*Euphytica* 148: 311-318, 2006). The identification of alleles and DM-resistance conferring alleles as set forth herein, allows the use of any other such markers in the same region and genetically linked (in linkage disequilibrium) therewith.

The genomic region, alleles, and polymorphic markers identified herein can be mapped relative to any publicly available physical or genetic map to place the region described herein on such map. One of skill in the art would also understand that additional polymorphic nucleic acids as described herein that are genetically linked to an allele associated with resistance to DM in spinach and that map within about 40 cM, 20 cM, 10 cM, 5 cM, or 1 cM of an allele or a markers associated with resistance to DM in spinach may also be used.

The above markers and allelic states are therefore exemplary. One of skill in the art would recognize how to identify spinach plants with other polymorphic nucleic acid markers and allelic states thereof related to resistance to DM in spinach consistent with the present disclosure. One of skill the art would also know how to identify the allelic state of other polymorphic nucleic acid markers located in the genomic region(s) or linked to an allele or other markers identified herein, to determine their association with resistance to DM in spinach.

Genomic Regions, Polymorphic Nucleic Acids, and Genetic Background Associated with Recipient Parent.

Described herein are markers for use in identifying the presence or absence of a resistance allele. In accordance with the invention, markers in the spinach genome that are not associated with or lack significant genetic linkage to the resistance locus allow the selection of genetic background. One example of background selection is recovery of the genome of a recipient parent in a recurring backcross scheme, an example of which is provided herein. In recurrent selection, multiple rounds of mating between sibs carrying favorable characteristics are carried out and selections made of progeny, allowing introduction of DM resistance-conferring alleles along with genetic diversity into a pedigree while maintaining favorable attributes of one or more elite parent. Examples of markers for spinach distributed genome-wide and that may be used in production of plants according to the methods of the invention are described in, for example, Khattak et al. (*Euphytica* 148: 311-318, 2006). The identification of DM resistance-conferring alleles set forth herein, concurrent with background selection, allows the use of any marker in the same genetic interval and any marker in other genetic intervals of genomic fragments.

Introgression of a Genomic Locus Associated with Resistance to DM in Spinach

Provided herein are spinach plants (*S. oleracea*) comprising a combination of alleles that confer broad-spectrum resistance to DM and methods of obtaining the same. In accordance with the invention, marker-assisted introgression involves the transfer of a chromosomal region, defined by one or more markers, from one germplasm to a second germplasm. Offspring of a cross that contain an introgressed genomic region can be identified by the combination of markers characteristic of the desired introgressed genomic region from a first germplasm (e.g., germplasm with resistance to DM) and both linked and unlinked markers characteristic of the desired genetic background of a second germplasm.

Markers that are linked and/or either immediately adjacent to a locus comprising an identified DM-resistance allele or locus as described herein that permit introgression of an allele or locus in the absence of extraneous linked DNA from the source germplasm containing the allele or locus are provided herewith. Those of skill in the art will appreciate that when seeking to introgress a smaller genomic region comprising an allele or locus associated with resistance to DM described herein, any of the telomere proximal or centromere proximal markers that are immediately adjacent to a larger genomic region comprising the allele or locus can be used to introgress that smaller genomic region.

Spinach plants or germplasm comprising such an introgressed region that is associated with resistance to DM wherein at least 10%, 25%, 50%, 75%, 90%, or 99% of the remaining genomic sequences carry markers characteristic of plant or germplasm that otherwise or ordinarily comprise a genomic region associated with another phenotype, are therefore provided in specific embodiments. Furthermore, spinach plants comprising an introgressed region where closely linked regions adjacent and/or immediately adjacent to a genomic region, allele or locus, and/or markers provided herewith that comprise genomic sequences carrying markers characteristic of spinach plants or germplasm that otherwise or ordinarily comprise a genomic region associated with the phenotype are also provided.

Molecular Assisted Breeding Techniques

Genetic markers that can be used in the practice of the present invention include, but are not limited to, Restriction Fragment Length Polymorphisms (RFLP), Amplified Fragment Length Polymorphisms (AFLP), Simple Sequence Repeats (SSR), simple sequence length polymorphisms (SSLPs), Single Nucleotide Polymorphisms (SNP), Insertion/Deletion Polymorphisms (Indels), Variable Number Tandem Repeats (VNTR), Random Amplified Polymorphic DNA (RAPD), isozymes, and others known to those skilled in the art. Marker discovery and development in crops provides the initial framework for applications to marker-assisted breeding activities (U.S. Patent Pub. Nos.: 2005/0204780; 2005/0216545; 2005/0218305; and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single-strand conformational polymorphism (Orita et al. *Genomics*, 8(2):271-278, 1989), denaturing gradient gel electrophoresis (Myers EPO 0273085, 1985), or cleavage fragment length polymorphisms (Life Technologies, Inc., Gathersberg, Md. 20877), although the widespread availability of DNA sequencing machines often makes it easier to just sequence amplified products directly. Once the polymorphic sequence difference is known, rapid assays can be designed for progeny testing, typically involving some version of PCR amplification of specific alleles (PASA, Sommer et al., *Biotechniques* 12(1):82-87, 1992), or PCR amplification of multiple specific alleles (PAMSA, Dutton et al., *Biotechniques* 11(6):700-702, 1991).

As a set, polymorphic markers serve as a useful tool for fingerprinting plants to inform the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a spinach plant a genotype associated with resistance to DM, identify a spinach plant with a genotype associated with resistance to DM, and to select a spinach plant with a genotype associated with resistance to DM. In certain embodiments of methods of the invention, polymorphic nucleic acids can be used to produce a spinach plant that comprises in its genome a combination of alleles associated with resistance to DM. In certain embodiments of the invention, polymorphic nucleic acids can be used to breed progeny spinach plants comprising a combination of alleles associated with resistance to DM.

Certain genetic markers may include "dominant" or "codominant" markers. "Codominant" markers reveal the presence of two or more alleles (two per diploid individual). "Dominant" markers reveal the presence of only a single allele. Markers are preferably inherited in a codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e., for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with a DM resistance phenotype.

As used herein, nucleic acid analysis methods include, but are not limited to, PCR-based detection methods (e.g., TaqMan assays), microarray methods, mass spectrometry-based methods and/or nucleic acid sequencing methods, including whole-genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. *Cold Spring Harbor Symp. Quant. Biol.* 51:263-273, 1986; European Patent No. 50,424; European Patent No. 84,796; European Patent No. 258,017; European Patent No. 237,362; European Patent No. 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613; 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981; and 7,250,252 all of which are incorporated herein by reference in their entireties. However, the compositions and methods of the present invention can be used in conjunction with any polymorphism typing method to type polymorphisms in genomic DNA samples. These genomic DNA samples used include, but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944, where a sequence of interest is amplified and hybridized to probes, followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523, 2003; Cui et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group that can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to the sequence of the locus of genomic DNA which flanks a region containing the polymorphism to be assayed. Following amplification of the region of the genome containing the polymorphism, the PCR product is mixed with the third oligonucleotide (called an extension primer), which is designed to hybridize to the amplified DNA adjacent to the polymorphism in the presence of DNA polymerase and two differentially labeled dideoxynucleoside triphosphates. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated, and only one of the two labels will be detected. Heterozygous samples have both alleles present and will direct incorporation of both labels (into different molecules of the extension primer), and thus both labels will be detected.

In another method for detecting polymorphisms, SNPs and Indels can be detected by methods disclosed in U.S. Pat. Nos. 5,210,015; 5,876,930; and 6,030,787, in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism, while the hybridization probe hybridizes to polymorphism-containing sequence within the amplified PCR product. In the subsequent PCR cycle, a DNA polymerase with 5'→3' exonuclease activity cleaves the probe and separates the reporter dye from the quencher dye resulting in increased fluorescence of the reporter.

In another embodiment, an allele or locus of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R.F. Service *Science* 311:1544-1546, 2006.

Markers used in accordance with the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of alleles or loci.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which spinach plants can be regenerated, plant calli, plant clumps and plant cells that are intact in plants or parts of plants such as pollen, flowers, seeds, leaves, stems, and the like.

As used herein, "DM" or "downy mildew" refers to a disease of plants, such as spinach, caused by a pathogen from the genus *Peronospora*, in particular *Peronospora farinosa f.* sp. *Spinaciae* (Pfs).

As used herein, "race" refers to an officially designated strain of *Peronospora farinosa f.* sp. *spinaciae* (Pfs) that can cause DM. As used herein, "isolate" refers to a newly occurring strain of *Peronospora farinosa f.* sp. *spinaciae* (Pfs) that can cause DM, and has not yet been officially named. A spinach plant with resistance to DM according to the present invention carries a combination of alleles selected from A, C, and Vt. The DM resistance may be to one or more known races of *Peronospora farinosa f.* sp. *spinaciae*, or may be to one or more isolates of *Peronospora farinosa f.* sp. *spinaciae*. In another embodiment, a plant of the invention may be defined as resistant to at least *Peronospora farinosa f.* sp. *spinaciae* Pfs 7, 8, 10, 11, 12, 13, and/or 14.

As used herein, the terms "pedigree," "population," and "progeny" mean a collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "resistance" means evasion and/or reduction of pathogen infection by plant innate immunity, which can be shown by the absence and/or reduction of disease symptoms when compared to a susceptible plant.

As used herein, the term "susceptible" means the infection of a plant by a pathogen, resulting in disease symptoms.

As used herein, the term "compatible interaction" means the infection of a susceptible plant by a pathogen, resulting in disease symptoms.

As used herein, the term "incompatible interaction" means the evasion and/or reduction of infection of a resistant plant by a pathogen, which can be shown by the absence and/or a reduction of disease symptoms.

As used herein, the term "genotype" means the specific allelic makeup of a plant.

As used herein, the term "heterozygous phase" means a diploid plant, such as spinach, that carries two distinct copies of an allele.

As used herein, the term "homozygous phase" means a diploid plant, such as spinach, that carries two identical copies of an allele.

As used herein, the term "introgressed," when used in reference to a genetic locus, refers to a genetic locus that has been introduced into a new genetic background, such as through backcrossing. Introgression of a genetic locus can therefore be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, the term "denoting" when used in reference to a plant genotype refers to any method whereby a plant is indicated to have a certain genotype. This includes any means of identification of a plant having a certain genotype. Indication of a certain genotype may include, but is not limited to, any entry into any type of written or electronic medium or database whereby the plant's genotype is provided. Indications of a certain genotype may also include, but are not limited to, any method where a plant is physically marked or tagged. Illustrative examples of physical marking or tags useful in the invention include, but are not limited to, a barcode, a radio-frequency identification (RFID), a label, or the like.

Deposit Information

A deposit was made of at least 2500 seeds of *Spinacia oleracea* accessions designated SMBS011-1162M, SMB-66-1143M, and SSB-66-1131M. The deposits were made with the American Type Culture Collection (ATCC), 10801 University Boulevard, Manassas, Va. 20110-2209 USA. The deposits were assigned ATCC Accession Nos. PTA-120472, PTA-12486, and PTA-12041, respectively. The dates of deposit of these accessions were Jul. 17, 2013, Feb. 2, 2012, and Aug. 19, 2011, respectively. Access to the deposits will be available during the pendency of the application to persons entitled thereto upon request. The deposits will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLES

The following disclosed embodiments are merely representative of the invention which may be embodied in various forms. Thus, specific structural, functional, and procedural details disclosed in the following examples are not to be interpreted as limiting.

Example 1

Identification of Novel Resistance to DM Races in *Spinacia oleracea*

A screen was performed on *S. oleracea* germplasm using the disease assay described in Example 5. *S. oleracea* accessions in an internal genebank were screened. In addition, publicly available spinach hybrids that were either fully susceptible, or carried a combination of resistance specificities were included in the trial as susceptible and resistance checks. Infection was performed with *Peronospora farinosa f.* sp. *spinaciae* (Pfs) races 7, 8, and 10-14 to complement historic data on races 1-6. Race 9 is no longer present in the field. In addition to strains with a race designation, a resistance-breaking isolate, collected in California (US) in the spring of 2013 was included. This isolate is currently referred to as UA4712 by the International Working Group on Peronospora and is a probable candidate for race Pfs 15.

The response of control entries to infection is presented in Table 1 and is consistent with data published elsewhere (Correll et al., *Eur J Plant Pathol* 129:193-205, 2011). Despite the contribution of resistance specificities by both parents, all commercial hybrid checks included in the trial failed to respond with resistance to all isolates. For example, variety Lion is susceptible to race 10, Lazio is susceptible to races 11-14, and Pigeon is susceptible to race 14. Resistance to both races 10 and 14 was not observed in any single hybrid, and a combination of resistance to races 13 and 14 was only observed for the hybrid Lion.

Among the *S. oleracea* accessions in the internal genebank, three lines were found to have a complementary combination of resistances. Inbred line SMBS011-1162M, carrying an allele identified as allele A, was resistant to multiple races, including races 13 and 14. A second inbred line, SSB-66-1131M, included an allele designated Vt, was found to be resistant to races 1-13. A final inbred line, SMB-66-1143M, which includes an allele identified as allele C, was shown to be resistant to new isolate UA4712, in addition to races 1-10. Each of the identified alleles were found to confer DM resistance to different combinations of races.

TABLE 1

Phenotypic response of control and experimental entries to infection by Pfs races 1-14 and isolate UA4712.

| | COMMERCIAL HYBRIDS | | | | | | | | | | LINES | | |
|---|---|---|---|---|---|---|---|---|---|---|---|---|---|
| Accession | | | | | | | | | | | A (SMBS011- | Vt (SSB-66- | C (SMB-66- |
| Race | Viroflay | Resistoflay | Clermont | Campania | Boeing | Califlay | Whale | Lion | Lazio | Pigeon | 1162M) | 1131M) | 1143M) |
| Pfs 1 | S | R | R | R | R | R | R | R | R | R | R | R | R |
| Pfs 2 | S | R | R | R | R | S | S | R | R | R | S | R | R |
| Pfs 3 | S | S | R | R | R | R | R | R | R | R | R | R | R |
| Pfs 4 | S | S | R | R | R | S | S | R | R | R | S | R | R |
| Pfs 5 | S | S | S | R | R | R | R | R | R | R | R | R | R |
| Pfs 6 | S | S | S | S | R | S | S | R | R | R | S | R | R |
| Pfs 7 | S | S | S | R | R | S | S | R | R | R | R | R | R |
| Pfs 8 | S | S | S | S | S | R | R | R | R | R | R | R | R |
| Pfs 10 | S | S | S | S | S | S | S | S | R | R | S | R | R |
| Pfs 11 | S | S | S | R | R | R | R | R | S | R | R | R | S |
| Pfs 12 | S | S | S | S | S | R | R | R | S | R | R | R | S |
| Pfs 13 | S | S | S | S | R | S | S | R | S | R | R | R | S |
| Pfs 14 | S | S | S | S | S | R | R | R | S | S | R | S | S |
| UA4712 | | | | | | | | | | | S | S | R |

S, susceptible response, with an average percentage of sporulating leaf surface estimated above 85%;
R, resistance, demonstrated by no or little (<3%) sporulation.

Example 2

Mapping Resistance to DM

Irish et al. (2008) identified a co-dominant marker, designated Dm-1, which was closely linked to the resistance locus RPF1 from *S. oleracea*. The genetic distance between Dm-1 and RPF1 was estimated to be 1.7 cM. Further efforts to fine-map the Dm-1 marker relative to the RPF1 locus generated sequence resources in the vicinity of the Dm-1 marker, but did not result in cloning RPF1 (Yang et al., Initial fine-mapping of the spinach downy mildew resistance locus RPF1, University of Arkansas, 2013, 102 pages; 1536814). Given the absence of a causal polymorphism and the distance between Dm-1 and RPF1, association may be lost during backcrossing or recurrent selection. Therefore, markers flanking resistance on both sides were needed for tracking resistance alleles and further fine-mapping.

Spinach lines carrying one of the three resistance alleles, A, Vt, or C, were individually crossed to a line that exclusively harbored resistance to races Pfs 1-4. Resistance to most races is inherited in a dominant fashion, based on the absence of symptoms upon infection of F1 individuals with races that differentiate between resistance from both parents. In contrast, resistance from allele A to races 7 and 13 appears to be recessive. F3 families were obtained through single seed descent from the separate bi-parental F1 crosses and screened phenotypically. The disease assay included 74 F3 families segregating for allele A, which were infected with Pfs race 8; 107 F3 families segregating for allele Vt challenged with races 7, 10, and 12; and 40 F3 families segregating for allele C, which were inoculated with race 10. Interestingly, when Vt-derived families demonstrated resistance to one race, immunity to the other two races was also observed.

Based on public information, the likely position of sequence scaffolds designated SF34732, SF59002, SF62749, SF63815, SF90906, SF95487, and SF178637 co-located with DM resistance. Examples of nucleotide sequences corresponding to alleles C, A, and Vt conferring resistance to DM are provided as SEQ ID NOs:1-25. Additionally, polymorphisms between individual alleles of scaffolds are shown in FIG. 3. Single nucleotide polymorphisms (SNPs) derived from these scaffolds were selected based on being polymorphic in one or more mapping populations. The SNPs were converted to TaqMan (TM) assays and used for genotyping F2 individuals of the respective F3 families of each population. Linkage disequilibrium was tested, and the genetic distances among SNPs and phenotypes were estimated using Joinmap (Stam, *Plant J* 3:739-744, 1993). Association analysis confirmed linkage of sequence scaffolds and resistance by assembly of single groups. This result was found to be independent of the source or race used for mapping (FIG. 1). Observed recombination frequencies and derived genetic distances varied due to the distinct sample size of each population. Scaffolds SF59002 and SF95487 appeared to co-segregate in every population. The order of scaffolds and genetic markers was consistent for populations segregating for allele Vt or allele C. However, the exact position of SF62749 relative to, for example, scaffolds SF59002 and SF90906 remains ambiguous. Finally, converted and mapped SSR markers, which were published by Khattak et al. (*Euphytica* 148:311-318, 2006), identified the linkage group as public LG6.

Example 3

Quantitative Effects of DM Resistance Alleles

The genotype and phenotypes collected in Example 2 were used in a quantitative analysis with mapQTL, applying standard interval mapping settings (Van Ooijen, 1996). A major locus for resistance to *Peronospora farinosa* f. sp. *spinaciae* race 8 was detected in the mapping population segregating for allele A. Evidenced by a LOD peak of 57.51, the trait was highly associated with markers derived from scaffolds SF59002, SF95487, and SF63815 (Table 2). The locus appeared to have a major effect, explaining 97.2% of the observed variance.

TABLE 2

Quantitative analysis of resistance allele A to Pfs race 8.

| map | lod | iter | mu_A | mu_H | mu_B | var | % expl | add | dom | locus |
|---|---|---|---|---|---|---|---|---|---|---|
| — | — | — | — | — | — | — | — | — | — | — |
| 0 | 40.53 | 4 | 94.4444 | 50 | 2.63158 | 92.0657 | 92 | 45.9064 | 1.46199 | SF90906a |
| 0.7 | 46.42 | 4 | 97.0588 | 50 | 2.63158 | 63.8022 | 94.4 | 47.2136 | 0.154799 | SF90906b |
| 1.4 | 57.51 | 4 | 100 | 50 | 2.63158 | 32.0057 | 97.2 | 48.6842 | −1.31579 | SF59002 |
| 1.4 | 57.51 | 4 | 100 | 50 | 2.63158 | 32.0057 | 97.2 | 48.6842 | −1.31579 | SF95487 |
| 1.4 | 57.51 | 4 | 100 | 50 | 2.63158 | 32.0057 | 97.2 | 48.6842 | −1.31579 | SF63815 |
| 5.7 | 31.74 | 4 | 94.1176 | 50 | 2.77778 | 159.093 | 86.1 | 45.6699 | 1.55229 | SF62749 |

A second analysis with source Vt (SSB-66-1131M) for resistance to Pfs races 7, 10, and 12 also identified a resistance locus (Tables 3, 4, and 5). Independent of the isolate used, the locus appeared to be strongly linked to scaffolds SF95487 and SF59002, evident by a LOD peak of 91.81. This locus had a major effect, explaining nearly all phenotypic variance. Strikingly, the loci identified in resistant sources A (SMBS011-1162M) and Vt (SSB-66-1131M) were collinear.

TABLE 3

Quantitative analysis of resistance allele Vt to Pfs race 7.

| map | lod | iter | mu_A | mu_H | mu_B | var | % expl | add | dom | locus |
|---|---|---|---|---|---|---|---|---|---|---|
| — | — | — | — | — | — | — | — | — | — | — |
| 0 | 24.43 | 4 | 88 | 52.7273 | 9.25926 | 408.188 | 65.1 | 39.3704 | 4.09764 | SF34732a |
| 0.6 | 25.6 | 4 | 88.4615 | 51.8519 | 9.25926 | 388.21 | 66.8 | 39.6011 | 2.99145 | SF34732b |
| 11.7 | 91.81 | 4 | 98.0769 | 50 | 0 | 22.4659 | 98.1 | 49.0385 | 0.961538 | SF95487 |
| 11.7 | 91.81 | 4 | 98.0769 | 50 | 0 | 22.4659 | 98.1 | 49.0385 | 0.961538 | SF59002 |
| 13.8 | 55.39 | 4 | 94.4444 | 50.9259 | 1.92308 | 107.703 | 90.8 | 46.2607 | 2.74217 | SF90906 |
| 19.8 | 31.02 | 4 | 89.6552 | 51.0638 | 11.2903 | 307.4 | 73.7 | 39.1824 | 0.591082 | SF62749 |

TABLE 4

Quantitative analysis of resistance allele Vt to Pfs race 10.

| map | lod | iter | mu_A | mu_H | mu_B | var | % expl | add | dom | locus |
|---|---|---|---|---|---|---|---|---|---|---|
| — | — | — | — | — | — | — | — | — | — | — |
| 0 | 24.43 | 4 | 88 | 52.7273 | 9.25926 | 408.188 | 65.1 | 39.3704 | 4.09764 | SF34732a |
| 0.6 | 25.6 | 4 | 88.4615 | 51.8519 | 9.25926 | 388.21 | 66.8 | 39.6011 | 2.99145 | SF34732b |
| 11.7 | 91.81 | 4 | 98.0769 | 50 | 0 | 22.4659 | 98.1 | 49.0385 | 0.961538 | SF95487 |
| 11.7 | 91.81 | 4 | 98.0769 | 50 | 0 | 22.4659 | 98.1 | 49.0385 | 0.961538 | SF59002 |
| 13.8 | 55.39 | 4 | 94.4444 | 50.9259 | 1.92308 | 107.703 | 90.8 | 46.2607 | 2.74217 | SF90906 |
| 19.8 | 31.02 | 4 | 89.6552 | 51.0638 | 11.2903 | 307.4 | 73.7 | 39.1824 | 0.591082 | SF62749 |

TABLE 5

Quantitative analysis of resistance allele Vt to Pfs race 12.

| map | lod | iter | mu_A | mu_H | mu_B | var | % expl | add | dom | locus |
|---|---|---|---|---|---|---|---|---|---|---|
| — | — | — | — | — | — | — | — | — | — | — |
| 0 | 24.43 | 4 | 88 | 52.7273 | 9.25926 | 408.188 | 65.1 | 39.3704 | 4.09764 | SF34732a |
| 0.6 | 25.6 | 4 | 88.4615 | 51.8519 | 9.25926 | 388.21 | 66.8 | 39.6011 | 2.99145 | SF34732b |
| 11.7 | 91.81 | 4 | 98.0769 | 50 | 0 | 22.4659 | 98.1 | 49.0385 | 0.961538 | SF95487 |
| 11.7 | 91.81 | 4 | 98.0769 | 50 | 0 | 22.4659 | 98.1 | 49.0385 | 0.961538 | SF59002 |
| 13.8 | 55.39 | 4 | 94.4444 | 50.9259 | 1.92308 | 107.703 | 90.8 | 46.2607 | 2.74217 | SF90906 |
| 19.8 | 31.02 | 4 | 89.6552 | 51.0638 | 11.2903 | 307.4 | 73.7 | 39.1824 | 0.591082 | SF62749 |

A study for resistance from allele C was performed with Pfs race 10. Similar to previous results, a major locus for resistance appeared to be significantly associated with scaffolds SF34732 and SF63815 (Table 6).

TABLE 6

Quantitative analysis of resistance allele C to Pfs race 10.

| map | lod | iter | mu_A | mu_H | mu_B | var | % expl | add | dom | locus |
|---|---|---|---|---|---|---|---|---|---|---|
| 0 | perfect fit | 3 | 100 | 50 | 0 | 0 | 100 | 50 | 0 | SF34732 |
| 0 | perfect fit | 3 | 100 | 50 | 0 | 0 | 100 | 50 | 0 | SF63815 |
| 1.3 | 28.02 | 4 | 100 | 46.6667 | 0 | 58.3333 | 96 | 50 | −3.33333 | SF95487 |
| 1.3 | 28.02 | 4 | 100 | 46.6667 | 0 | 58.3333 | 96 | 50 | −3.33333 | SF59002 |
| 2.6 | 22.3 | 4 | 100 | 46.4286 | 6.25 | 112.723 | 92.3 | 46.875 | −6.69643 | SF90906 |
| 8.4 | 12.19 | 4 | 100 | 47.2222 | 8.33333 | 361.111 | 75.4 | 45.8333 | −6.94444 | SF62749 |
| 22.1 | 6.14 | 4 | 96.6667 | 47.2222 | 28.5714 | 724.504 | 50.7 | 34.0476 | −15.3968 | SF178637 |

DM resistance mapped to Chromosome 6 independent of the source or isolate used. The resistance loci were delineated by common markers, on the distal position typically sequence scaffolds SF34732 and SF63815 and on the proximal position typically sequence scaffolds SF59002, SF95487 and SF90906.

Example 4

Deployment of Resistance Alleles A, Vt, and C in Hybrids

Figure 2A:
FIG. 2A and FIG. 2B: Show possible breeding methods for development of hybrids and three-way hybrids.
Figure 2A:
Figure 2A:

The resistance alleles A, C and Vt were introduced into a susceptible hybrid. The inbred SMBS011-1162M was used as a donors for allele A, the line SSB-66-1131M for Vt, and for allele C, SMB-66-1143M was used as a source. Each of the alleles was introgressed separately into both inbred parents of the susceptible hybrid, following breeding methods known in the art. Next, a first spinach plant which is homozygous for allele A (A/A) was crossed to a second spinach plant (C/C) to generate a hybrid F1 which was heterozygous for alleles A and C (FIG. 2A). This hybrid was referred to as Single Hybrid A, or as F1(A/C). F1(A/C) was screened with known races and isolate UA4712 of *Peronospora farinosa f.* sp. *spinaciae*, as described in Example 5. The hybrid was found to be resistant to all Pfs races, with the exception of race 13 (Table 7). Hybrid A is also resistant to the newly emerging isolate UA4712.

Hybrid B carrying alleles C and Vt (FIG. 2B) was screened as described and found to be resistant to all Pfs races except Pfs 14 (Table 7). This is important, as Pfs race 14 does not occur in Europe. A combination of alleles C and Vt in a spinach plant provides a fully resistant variety for the European market.

Hybrid C with alleles A and Vt was resistant to all Pfs races except isolate UA4712 (Table 7). This is also significant, since the distribution of a new isolate is initially limited to few locations. F1(A/Vt) is resistant to all currently named Pfs races.

Figure 2B:
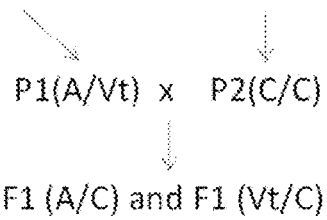
Figure 2B:
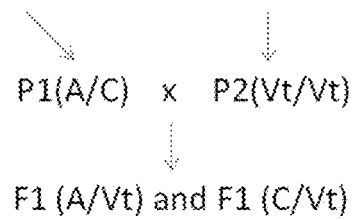
Figure 2B:
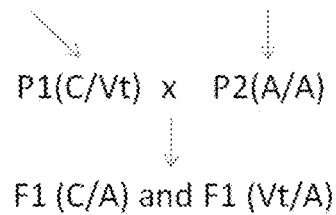

In addition to biparental hybrids, three-way hybrids were generated. Three-way hybrids are produced by crossing an F1 seed parent to an inbred parent P2. The F1 seed parent results from a cross between two near-isogenic lines of P1, each carrying a distinct resistance allele. The inbred parent P2 carries a third, complementary allele. A three-way hybrid allows the deployment of all three identified alleles in a mixed population of diploid hybrid plants. Three versions of the 3-way hybrid are possible (FIG. 2B). Each cross results in a population of hybrid plants with resistance to all known Pfs races and isolate UA4712. However, the frequency of each allele will depend on how the three-way cross is structured.

Novel resistance originating from the genetic variety contained within cultivated spinach, *Spinacia oleracea* was identified. This resistance is surprising because genetic diversity in cultivated crops is typically narrow (Fernie et al., *Curr. Opinion Pl.* Biol. 9:196-202, 2006). The identification of the three unique resistance alleles, A, Vt, and/or C, in the three spinach lines provides for race-specific DM resistance breeding, with only intra-specific *S. oleracea* crosses. Additionally, these alleles allow stacking of resistance in single hybrid combinations that are unsurpassed in combining novel attributes, including resistance to all known Pfs races, to the new isolate UA4712, or resistance to all described European DM populations. Markers associated with the three resistance alleles allow introduction of the described and other DM-resistance alleles in any cultivated spinach hybrid. Finally, a three-way hybrid method is disclosed to allow for the development of additional DM resistant varieties.

TABLE 7

Phenotypic response of testcrosses to infection of leaf discs by Pfs races 1-8, 10-14 and isolate UA4712

| TEST CROSS | Pfs 1 | Pfs 2 | Pfs 3 | Pfs 4 | Pfs 5 | Pfs 6 | Pfs 7 | Pfs 8 | Pfs 10 | Pfs 11 | Pfs 12 | Pfs 13 | Pfs 14 | UA4712 |
|---|---|---|---|---|---|---|---|---|---|---|---|---|---|---|
| F1 (A/C) | R | R | R | R | R | R | R | R | R | R | R | S | R | R |
| F1 (C/Vt) | R | R | R | R | R | R | R | R | R | R | R | R | S | R |
| F1 (AxVt) | R | R | R | R | R | R | R | R | R | R | R | R | R | S |

"S" indicates a susceptible response.
"R" indicates resistance

Example 5

Assays for Screening Spinach Accessions for Resistance to DM

A test was utilized for screening spinach accessions for resistance to downy mildew (DM) that originated from the International Union for the Protection of New Varieties of Plants (UPOV). The "Protocol for Tests on Distinctness, Uniformity, and Stability of *Spinacia oleracea* L. Spinach,"

UPOV Code: SPINA_OLE, CPVO-TP/055/5 was adopted and into force on Feb. 27, 2013. The protocol is as follows:

Races of *Peronospora farinosa f.* sp. *spinaciae* are maintained on living host plants, obtainable from Naktuinbouw (P.O. Box 40, NL-2370 AA, Roelofarendsveen, Netherlands, naktuinbouw.com), or plant material with spores stored at −20° C. for a maximum of one year.

Execution of test: Growth stage of plants: First cotyledons/leaf, eleven-day-old plants; Temperature: 15° C. during day/12° C. during night; Light: 15 hours per day, after emergence; Growing method: In soil in pots or trays in a glasshouse or growth chamber.

Method of inoculation: Sporulating leaves, taken from host plants that were infected seven days before, are thoroughly rinsed with sterile tap water (maximum 150 ml water per 224 plants). The spore suspension is filtered through cheesecloth and sprayed on test plants until the inoculum covers the leaves but does not run off. 150 ml of suspension is enough for up to 3×224 plants. Spore density should be 20,000 to 100,000 conidia/ml water. The spore suspension should be used fresh. As spinach downy mildew is windborne, sporulating plants should be kept in closed containers or isolated chambers to prevent any cross-contamination.

Resistant controls are needed in each multiplication and in each test to ensure the race identity. Light and humidity conditions during seedling development and incubation are critical. Optimal humidity of approximately 80-90% RH allows plant growth and fungal growth; strong light inhibits spore germination and infection. The test should be carried out in wintertime with protection against direct sunshine. After inoculation, the plants should remain under plastic for three days. After this time, the plastic should be slightly raised during the daytime.

Duration of test: Multiplication harvest spores 7 days after inoculation; Sowing to inoculation: 11 days; Inoculation to reading: 10 days; Number of plants tested: 56 plants; Evaluation of infection: Resistance is usually complete; sometimes necrotic spots are visible as a result of infection. Susceptible plants show varying degrees of sporulation. Sporulation is visible as a grey covering on leaves, starting on the more humid abaxial side.

Differential varieties to identify races: Races Pfs: 1-8 and 10-13 of *Peronospora farinosa f.* sp. *spinaciae* are defined with a standard set of "differential varieties" according to Table 8.

TABLE 8

Differential varieties to identify races: Races Pfs: 1-8 and 10-13 of *Peronospora farinosa* f. sp. *spinaciae*.

| Differential variety | Pfs: 1 | Pfs: 2 | Pfs: 3 | Pfs: 4 | Pfs: 5 | Pfs: 6 | Pfs: 7 | Pfs: 8 | Pfs: 10 | Pfs: 11 | Pfs: 12 | Pfs: 13 |
|---|---|---|---|---|---|---|---|---|---|---|---|---|
| Viroflay | S | S | S | S | S | S | S | S | S | S | S | S |
| Resistoflay | R | R | S | S | S | S | S | S | S | S | S | S |
| Califlay | R | S | R | S | R | S | S | R | S | R | R | S |
| Clermont | R | R | R | R | S | S | S | S | S | S | S | S |
| Campania | R | R | R | R | R | S | R | S | S | R | S | S |
| Boeing | R | R | R | R | R | R | R | S | S | R | S | R |
| Lion | R | R | R | R | R | R | R | R | S | R | R | R |
| Lazio | R | R | R | R | R | R | R | R | R | S | S | S |

R, resistance present;
S, resistance absent (susceptible)

What is claimed is:

1. A *Spinacia oleracea* spinach plant of a cultivated variety comprising in its genome allele A, wherein allele A confers resistance to *Peronospora farinosa* f. sp. *Spinaciae* races 1, 3, 5, 7, 8, 11, 12, 13, and 14, wherein said plant comprises a DNA sequence selected from the group consisting of SEQ ID NO:2, SEQ ID NO:19, and SEQ ID NO:22, and comprises the DNA sequence of SEQ ID NO:5 or SEQ ID NO:10, and wherein a sample of seed comprising said allele A has been deposited under ATCC Accession No. PTA-120472.

2. A *Spinacia oleracea* spinach plant of a cultivated variety comprising in its genome a heterozygous combination of alleles that confers broad-spectrum resistance to *Peronospora farinosa* f. sp. *Spinaciae*, wherein the combination of alleles comprises two alleles selected from the group consisting of allele A, allele Vt, and allele C, wherein allele A confers resistance to *Peronospora farinosa* f. sp. *Spinaciae* races 1, 3, 5, 7, 8, 11, 12, 13, and 14 and wherein a plant comprising allele A comprises a DNA sequence selected from the group consisting of SEQ ID NO:2, SEQ ID NO:19, and SEQ ID NO:22, and comprises the DNA sequence of SEQ ID NO:5 or SEQ ID NO:10, wherein allele Vt confers resistance to *Peronospora farinosa* f. sp. *Spinaciae* races 1, 2, 3, 4, 5, 6, 7, 8, 10, 11, 12 and 13 and wherein a plant comprising allele Vt comprises a DNA sequence selected from the group consisting of SEQ ID NO:6, SEQ ID NO:8, SEQ ID NO:11, SEQ ID NO:14, and SEQ ID NO:17 and comprises the DNA sequence of SEQ ID NO: 20 or SEQ ID NO: 23, and wherein allele C confers resistance to *Peronospora farinosa* f. sp. *Spinaciae* races 1, 2, 3, 4, 5, 6, 7, 8, 10 and isolate UA4712, and wherein a plant comprising allele C comprises a DNA sequence selected from the group consisting of SEQ ID NO:1, SEQ ID NO:18, and SEQ ID NO:21 and comprises the DNA sequence of SEQ ID NO:4, SEQ ID NO:9, SEQ ID NO:12, and SEQ ID NO: 15, and wherein a sample of seed comprising said allele A, allele Vt, and allele C has been deposited under ATCC Accession No. PTA-120472, ATCC Accession No. PTA-12041, and ATCC Accession No. PTA-12486, respectively, and wherein said broad-spectrum resistance comprises resistance to at least 10 races of *Peronospora farinosa* f. sp. *spinaciae* (Pfs).

3. The spinach plant of claim 2, wherein the combination of alleles comprises:
   (a) alleles A and C;
   (b) alleles A and Vt; or
   (c) alleles C and Vt.

4. The spinach plant of claim 2, wherein the plant is resistant to:
   (a) at least *Peronospora farinosa* f. sp. *Spinaciae* races, 7, 8, 10, 11, 12, 14, and isolate UA4712;
   (b) at least *Peronospora farinosa* f. sp. *Spinaciae* races, 7, 8, 10, 11, 12, 13, and 14; or
   (c) at least *Peronospora farinosa* f. sp. *Spinaciae* races, 7, 8, 10, 11, 12, 13, and isolate UA4712.

5. The spinach plant of claim 1, wherein said plant is an inbred.

6. The spinach plant of claim 1, wherein said plant is a hybrid.

7. The spinach plant of claim 1, comprising recessive resistance to *Peronospora farinosa* f. sp. *Spinaciae* races 7 and 13.

8. A seed that produces the plant of claim 2.

9. A plant part of the plant of claim 2, wherein the plant is a leaf, stem, root, flower or cell.

10. A method of producing a seed of a spinach plant with broad-spectrum resistance to *Peronospora farinosa* f. sp. *Spinaciae* comprising:
(a) crossing a first spinach plant and a second spinach plant, wherein the first and second spinach plants collectively comprise at least two alleles selected from the group consisting of allele A, allele Vt, and allele C, wherein allele A confers resistance to *Peronospora farinosa* f. sp. *Spinaciae* races 1, 3, 5, 7, 8, 11, 12, 13, and 14 and wherein a plant comprising allele A comprises a DNA sequence selected from the group consisting of SEQ ID NO:2, SEQ ID NO:19, and SEQ ID NO:22, and comprises the DNA sequence of SEQ ID NO:5 or SEQ ID NO:10, wherein allele Vt confers resistance to *Peronospora farinosa* f. sp. *Spinaciae* races 1, 2, 3, 4, 5, 6, 7, 8, 10, 11, 12 and 13 and wherein a plant comprising allele Vt comprises a DNA sequence selected from the group consisting of SEQ ID NO:6, SEQ ID NO:8, SEQ ID NO:11, SEQ ID NO:14, and SEQ ID NO:17 and comprises the DNA sequence of SEQ ID NO: 20 or SEQ ID NO: 23, and wherein allele C confers resistance to *Peronospora farinosa* f. sp. *Spinaciae* races 1, 2, 3, 4, 5, 6, 7, 8, 10 and isolate UA4712 and wherein a plant comprising allele C comprises a DNA sequence selected from the group consisting of SEQ ID NO:1, SEQ ID NO:18, and SEQ ID NO:21 and comprises the DNA sequence of SEQ ID NO:4, SEQ ID NO:9, SEQ ID NO:12, and SEQ ID NO: 15; and wherein a sample of seed comprising said allele A, allele Vt, and allele C has been deposited under ATCC Accession No. PTA-120472, ATCC Accession No. PTA-12041, and ATCC Accession No. PTA-12486, respectively, and;
(b) obtaining at least a first seed resulting from said crossing that comprises a heterozygous combination of said alleles that confers broad-spectrum resistance to *Peronospora farinosa* f. sp. *Spinaciae*, wherein said broad-spectrum resistance comprises resistance to at least 10 races of *Peronospora farinosa* f. sp. *spinaciae*.

11. The method of claim 10, wherein the method further comprises obtaining a population of seed resulting from said crossing that comprises a heterozygous combination of said alleles that confers broad-spectrum resistance to *Peronospora farinosa* f. sp. *Spinaciae*.

12. The method of claim 10, wherein:
(a) the first spinach plant comprises allele A and the second spinach plant comprises allele C;
(b) the first spinach plant comprises allele A and the second spinach plant comprises allele Vt;
(c) the first spinach plant comprises allele C and the second spinach plant comprises allele Vt;
(d) the first spinach plant or the second spinach plant is homozygous for said allele A, allele Vt, or allele C; or
(e) the first spinach plant and the second spinach plant are homozygous for said two alleles selected from the group consisting of allele A, allele Vt, and allele C.

13. A seed produced by the method of claim 10.

14. The seed of claim 13, wherein:
(a) the first allele is allele A and the second allele is allele C;
(b) the first allele is allele A and the second allele is allele Vt; or
(c) the first allele is allele C and the second allele is allele Vt.

15. A method of introducing resistance to *Peronospora farinosa* f. sp. *Spinaciae* into a spinach plant comprising:
(a) crossing a first spinach plant comprising in its genome a first allele selected from the group consisting of A, Vt, and C, with a second spinach plant, wherein allele A confers resistance to *Peronospora farinosa* f. sp. *Spinaciae* races 1, 3, 5, 7, 8, 11, 12, 13, and 14 and wherein a plant comprising allele A comprises a DNA sequence selected from the group consisting of SEQ ID NO:2, SEQ ID NO:19, and SEQ ID NO:22, and comprises the DNA sequence of SEQ ID NO:5 or SEQ ID NO:10, wherein allele Vt confers resistance to *Peronospora farinosa* f. sp. *Spinaciae* races 1, 2, 3, 4, 5, 6, 7, 8, 10, 11, 12 and 13 and wherein a plant comprising allele Vt comprises a DNA sequence selected from the group consisting of SEQ ID NO:6, SEQ ID NO:8, SEQ ID NO:11, SEQ ID NO:14, and SEQ ID NO:17 and comprises the DNA sequence of SEQ ID NO: 20 or SEQ ID NO: 23, and wherein allele C confers resistance to *Peronospora farinosa* f. sp. *Spinaciae* races 1, 2, 3, 4, 5, 6, 7, 8, 10 and isolate UA4712 and wherein a plant comprising allele C comprises a DNA sequence selected from the group consisting of SEQ ID NO:1, SEQ ID NO:18, and SEQ ID NO:21 and comprises the DNA sequence of SEQ ID NO:4, SEQ ID NO:9, SEQ ID NO:12, and SEQ ID NO: 15; and wherein a sample of seed comprising said allele A, allele Vt, and allele C has been deposited under ATCC Accession No. PTA-120472, ATCC Accession No. PTA-12041, and ATCC Accession No. PTA-12486, respectively, and;
(b) selecting at least one progeny plant that comprises said first allele for resistance to *Peronospora farinosa* f. sp. *Spinaciae*, by detecting the presence in the genome of said progeny plant a DNA sequence selected from the group consisting of SEQ ID NOs:1-25.

16. The method of claim 15, wherein said crossing comprises producing a population of progeny plants.

17. The method of claim 15, comprising screening the progeny plants for the presence of at least two nucleic acid sequences selected from the group consisting of SEQ ID NOs: 1-25.

18. A plant produced by the method of claim 15.

19. A method of selecting a plant comprising a desired allele conferring resistance to *Peronospora farinosa* f. sp. *Spinaciae*, the method comprising detecting in the genome of said plant at least two nucleic acid sequences representing polymorphisms selected from the group consisting of SEQ ID NOs:1-24, wherein the presence of the nucleic acid sequences representing polymorphisms are indicative of the presence in the plant of at least two alleles conferring resistance to *Peronospora farinosa* f. sp. *Spinaciae* selected from the group consisting of alleles A, Vt, and C, wherein allele A confers resistance to *Peronospora farinosa* f. sp. *Spinaciae* races 1, 3, 5, 7, 8, 11, 12, 13, and 14 and wherein a plant comprising allele A comprises a DNA sequence selected from the group consisting of SEQ ID NO:2, SEQ ID NO:19, and SEQ ID NO:22, and comprises the DNA sequence of SEQ ID NO:5 or SEQ ID NO:10, wherein allele Vt confers resistance to *Peronospora farinosa* f. sp. *Spina-*

*ciae* races 1, 2, 3, 4, 5, 6, 7, 8, 10, 11, 12 and 13 and wherein a plant comprising allele Vt comprises a DNA sequence selected from the group consisting of SEQ ID NO:6, SEQ ID NO:8, SEQ ID NO:11, SEQ ID NO:14, and SEQ ID NO:17 and comprises the DNA sequence of SEQ ID NO: 20 or SEQ ID NO: 23, and wherein allele C confers resistance to *Peronospora farinosa* f. sp. *Spinaciae* races 1, 2, 3, 4, 5, 6, 7, 8, 10 and isolate UA4712 and wherein a plant comprising allele C comprises a DNA sequence selected from the group consisting of SEQ ID NO:1, SEQ ID NO:18, and SEQ ID NO:21 and comprises the DNA sequence of SEQ ID NO:4, SEQ ID NO:9, SEQ ID NO:12, and SEQ ID NO: 15; and wherein a sample of seed comprising said allele A, allele Vt, and allele C has been deposited under ATCC Accession No. PTA-120472, ATCC Accession No. PTA-12041, and ATCC Accession No. PTA-12486, respectively.

20. A plant selected by the method of claim 19.

21. A spinach cell or cell containing plant part of the plant of claim 2.

* * * * *

UNITED STATES PATENT AND TRADEMARK OFFICE
CERTIFICATE OF CORRECTION

| | |
|---|---|
| PATENT NO. | : 10,927,386 B2 |
| APPLICATION NO. | : 14/632871 |
| DATED | : February 23, 2021 |
| INVENTOR(S) | : Brugmans et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

Signed and Sealed this
Sixth Day of December, 2022

Katherine Kelly Vidal
*Director of the United States Patent and Trademark Office*